(12) United States Patent
Ying

(10) Patent No.: US 8,742,114 B2
(45) Date of Patent: Jun. 3, 2014

(54) NUCLEIC ACID DETECTIONS AND METHODS OF THEIR USE

(71) Applicant: Laiqiang Ying, Eugene, OR (US)

(72) Inventor: Laiqiang Ying, Eugene, OR (US)

(73) Assignee: Laiqiang Ying, Eugene, OR (US)

( * ) Notice: Subject to any disclaimer, the term of this patent is extended or adjusted under 35 U.S.C. 154(b) by 28 days.

(21) Appl. No.: 13/684,499

(22) Filed: Nov. 24, 2012

(65) Prior Publication Data

US 2013/0137875 A1    May 30, 2013

Related U.S. Application Data

(60) Provisional application No. 61/563,762, filed on Nov. 26, 2011.

(51) Int. Cl.
*C07D 215/00*    (2006.01)

(52) U.S. Cl.
CPC ................................. *C07D 215/00* (2013.01)
USPC ........................................................ 546/165

(58) Field of Classification Search
CPC ...................................................... C07D 215/00
See application file for complete search history.

*Primary Examiner* — Heidi Reese

(57) ABSTRACT

The invention describes the preparation and use of fluorescent stains for nucleic acids derived from unsymmetrical cyanine dyes, dimmers, trimers, or tetramers. In particular, the invention describes unsymmetric cyanine dyes, dimmers, trimer and tetramers having a water soluble substituent. The dyes of the invention possess superior fluorescent properties when complexed with nucleic acids, and have utility in any application which requires detection of nucleic acids, such as detection of nucleic acids in solution, in gels, in blots, in microarrays, and in bacteria and cells, and for use in analysis of cell structure, membrane integrity, and function. The presence of the water soluble substituent results in improved water soluability and stability, resulting in improved detection of nucleic acids.

11 Claims, 5 Drawing Sheets

FIG. 1 Normalized Fluorescence of Compound 39 and SYBR Gold in TBE Buffer Containing 25 μg/mL DNA
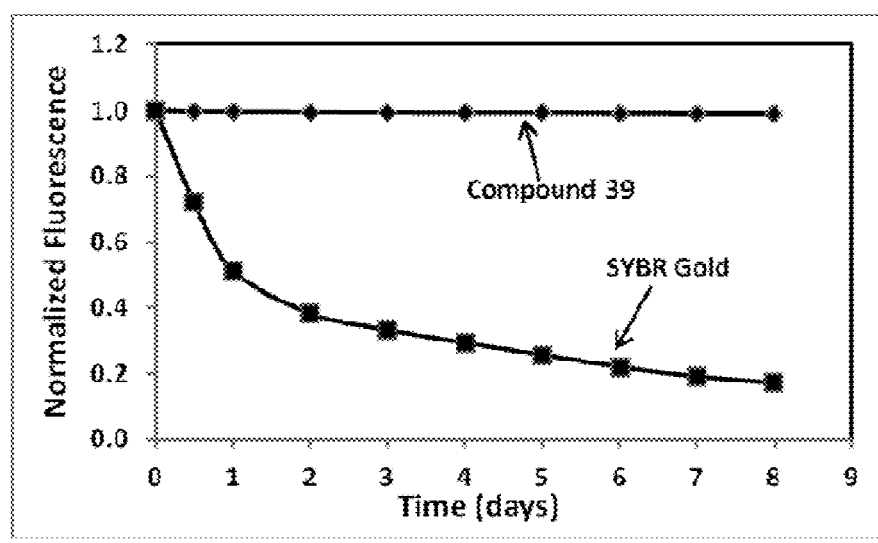

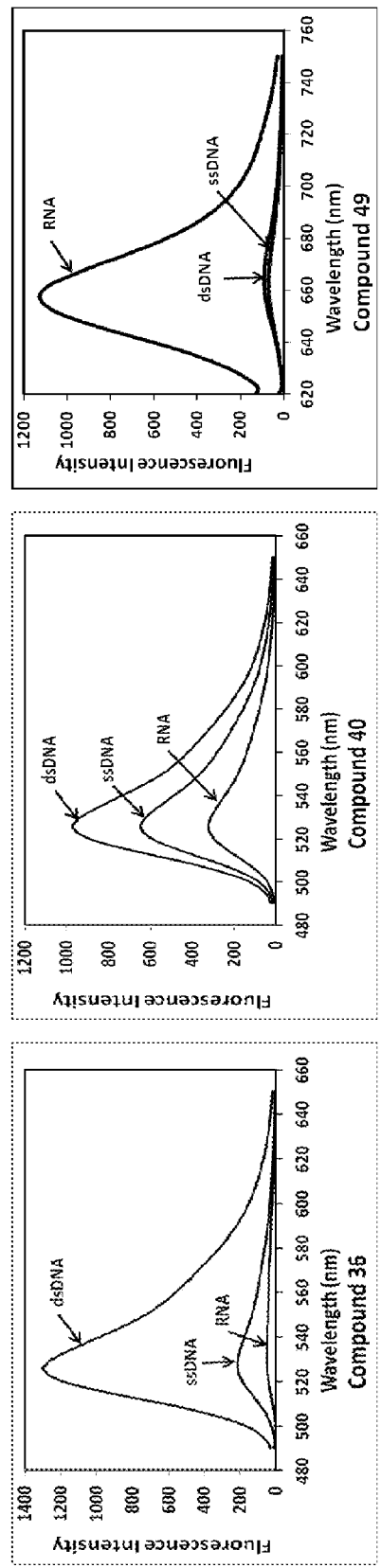
FIG. 2 Selectivity on dsDNA, ssDNA, and RNA of Compound (36), Compound (40) and Compound (49) in TE Buffer

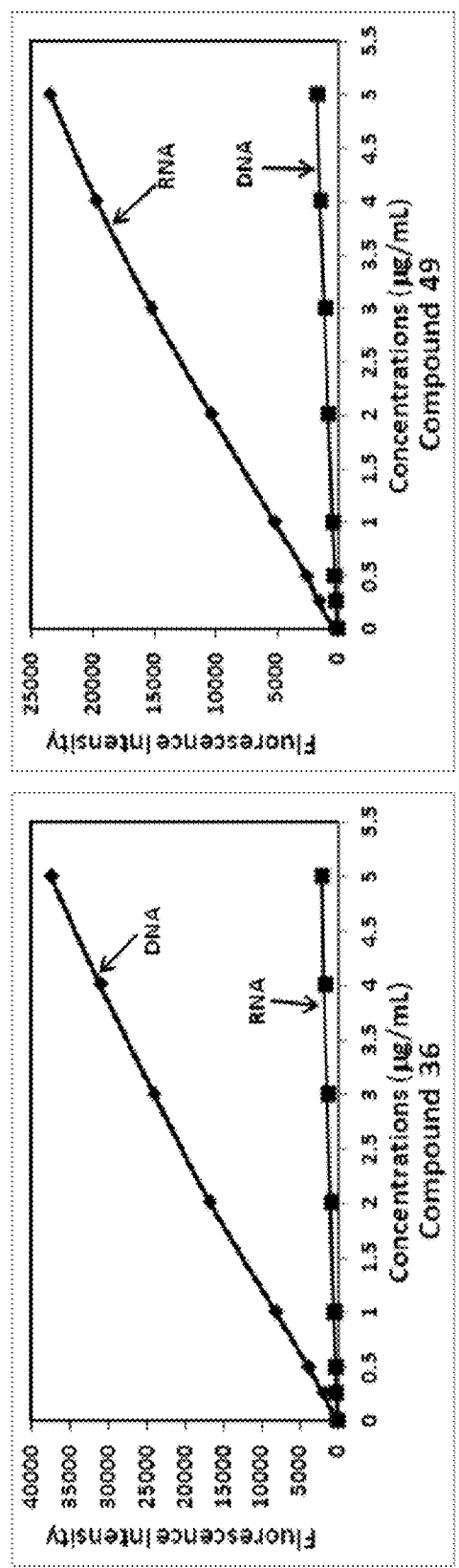
FIG. 3 Quantitation of DNA, and RNA in Solution

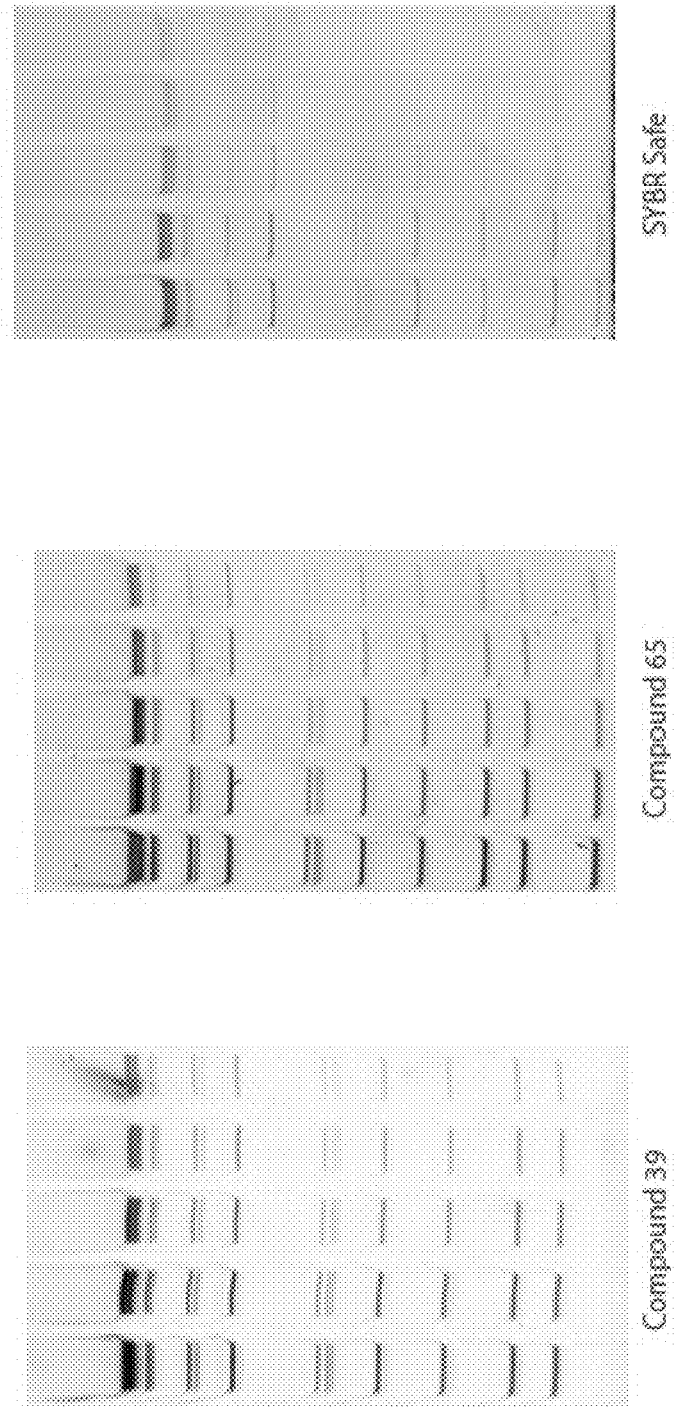
FIG. 4 Post-DNA Gel Staining

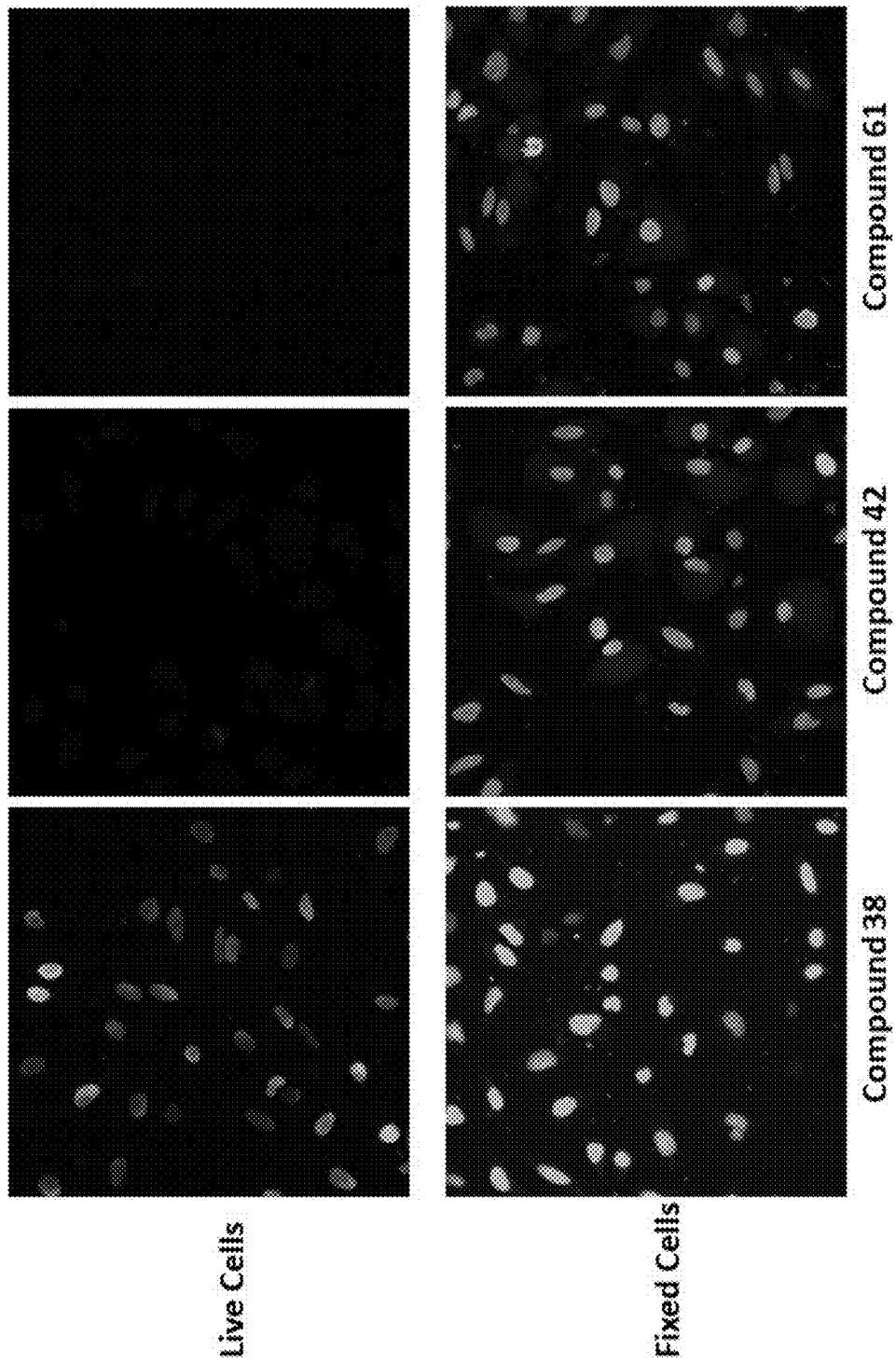
FIG. 5 Celluar Nucleic Acid Staining

NUCLEIC ACID DETECTIONS AND METHODS OF THEIR USE

CROSS-REFERENCE TO RELATED APPLICATIONS

This application claims the benefit of U.S. Provisional Application No. 61/563,762, filed Nov. 26, 2011, which application is incorporated herein by reference in its entirety.

BACKGROUND

Fluorescent dyes or stains have been widely used in biological detections in which the high detectability of fluorescence is desirable. By binding to a particular target in a biological sample enables the researcher to determine the presence or quantity of the target. Nucleic acids, such as DNA and RNA, are involved in the transmission of genetic information from one generation to the next, and the routine functions of live organisms. Nucleic acids are thus of interest and the objects of study. Fluorescent dyes that specifically bind to nucleic acids and form highly fluorescent complexes are useful tools for such study. These dyes can be used for detection of DNA or RNA in a variety of format, including in solution, in electrophoretic gels and blots, in microarray, dead or fixed cells, and live cells.

Several dyes are commercially available for detection of nucleic acids. Unsymmetrical cyanine dyes were described long before much was known about DNA, by Brooker, et al., J. AM. CHEM. SOC. 64, 199 (1942). The commercial dye Thiazole Orange has good applications in the quantitative analysis of immature blood cells or reticulocytes. U.S. Pat. No. 4,883,867 to Lee, et al. (1989); Lee, et al., Thiazole Orange: A New Dye for Reticulocyte Analysis, CYTOMETRY 7, 508 (1986). But, the limitation of Thiazole Orange is low detection sensitivity on nucleic acids. Ethidium bromide is the most widely used nucleic acid stain, and is commercially available from a number of suppliers. However, ethidium bromide is mutagenic, and its use requires significant care from the user to avoid contact with staining solutions, and special handing and waste disposal procedures (M. J. Waring, J. Mol. Biol. I 13, 269 (1965); McCann et al., Proc. Natl. Acad. Sci. USA, 72, 5135 (1975); and Fukunaga et al., Mutation Res. 127, 31 (19840)). PicoGreen is a stain selective for double stranded DNA and commercially available from Invitrogen; OliGreen is a stain useful for the quantitation of single stranded DNA and commercially available from Invitrogen; RiboGreen is a stain that is useful for quantitation of RNA in solution, and commercially available from Invitrogen; SYBR Green I is a stain selective for DNA and used for DNA gel stains and qPCR quantitation, and commercially available from Invitrogen; SYBR Gold is a high sensitive stain for both DNA and RNA, and commercially available from Invitrogen. These dyes are described in U.S. Pat. Nos. 5,436,134, 5,658, 751 and 5,863,753. However, these dyes have low water soluability and have to be predisolved in organic solvent such as DMSO or DMF; and also have limited stability in aqueous solution, and have to be used within 24 hours before losing sensitivity. Another asymmetric cyanine dye, SYBR Safe, is commercially available from Invitrogen as an alternative to SYBR Green I and Ethidium bromide due to its low mutagenicity. This dye is described in U.S. Pat. Nos. 7,727,716 and 7,977,057. However, this alternative dye is less water soluability and low sensitive than desired.

Development of fluorescent dyes with improved water soluability and stability or the making or the use thereof is desirable.

SUMMARY

Methods of designing, producing, or using a fluorescent dye suitable for useful applications, such as in solution detection and quantitation of nucleic acid, or in gel staining of nucleic acids. The dyes used for the invention are non-fluorescent or are minimally fluorescent by themselves, but become highly fluorescent in the presence of nucleic acids. In some embodiments, the dyes used for the invention become highly fluorescent in the presence of DNA or RNA. In some embodiments, the dyes used for the invention have high selectivity for double stranded DNA over single stranded DNA and RNA. In some embodiments, the dyes used for the invention have high selectivity for DNA over RNA. In some embodiments, the dyes used for the invention have high selectivity for RNA over DNA.

In some embodiments, the dyes used for the invention are substituted unsymmetric cyanine dyes with a side chain modified by a hydrophilic group to improve water soluability and stability. These dyes may have at least one feature, or all of the following features: relatively low "fluorescence background" (fluorescence in the absence of nucleic acids), if any, and ideally, no fluorescence background; relative low toxicity, and ideally, no toxicity; relatively high fluorescent signal strength; and relative high water soluability and stability in water. These dyes are preferably better as to at least one of these features than existing dyes, such as Ethidium Bromide, SYBR Green I, SYBR Gold, and SYBR Safe. The substituted unsymmetrical cyanine dyes have two aromatic ring groups joined by an unsaturated hydrocarbon chain containing one or more methane groups. The novel dyes generally have the formula:

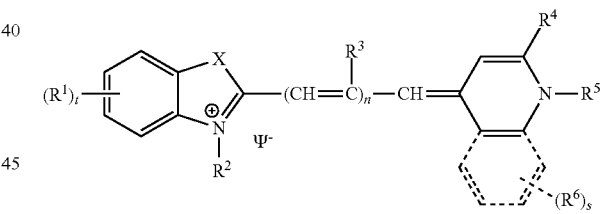

wherein:

X is O, S, C(CH$_3$)$_2$;

Each of $R^1$ and $R^6$ is independently hydrogen, carboxy, sulfo, phosphate, phosphonate, hydroxyl, halogen, CN, amino, alkylamino, dialkylamino, alkoxy, alkyl, substituted alkyl, aryl, heteroaryl, alkylaminocarbonyl, dialkylaminocarbonyl, alkylaminosulfonamide, dialkylamino-sulfonamide, alkyl group substituted by a carboxy, alkyl group substituted by a sulfo, alkyl group substituted by a phosphate, —Y—(CH$_2$)$_a$[O—(CH$_2$)$_b$]$_m$—O—Z, where Y is absent, O, NH(C=O), C(=O)NH, or S(=O)$_2$NH; Z is H, alkyl, carboxy, sulfo, phosphate; each of a and b is an integer from 1 to 4; m is an integer selected from 1 to 12; Each of t and s is an integer from 0 to 3;

$R^2$ is a substituted alkyl, unsubstituted alkyl, substituted arylalkyl, unsubstituted arylalkyl, substituted heteroalkyl, unsubstituted heteroalkyl, alkoxy, alkyl group substituted by a carboxy, a sulfo, a phosphate, an alkylamino, a dialkylamino, an alkylaminocarbonyl, a dialkylaminocarbonyl, an alkylaminosulfonamide, a dialkylaminosulfonamide, —(CH$_2$)$_a$[O—(CH$_2$)$_b$]$_m$—O—Z, where Z is H, alkyl, carboxy, sulfo, phosphate; each of a and b is an integer from 1 to 4; m is an integer selected from 1 to 12;

R$^3$ is H, substituted aryl, or unsubstituted aryl;

R$^4$ is H, substituted alkyl, unsubstituted alkyl, substituted heteroalkyl, unsubstituted heteroalkyl, substituted arylalkyl, unsubstituted arylalkyl, substituted aryl, unsubstituted aryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio;

R$^5$ is substituted alkyl, unsubstituted alkyl, substituted heteroalkyl, unsubstituted heteroalkyl, substituted arylalkyl, unsubstituted arylalkyl, substituted aryl, unsubstituted aryl, substituted cycloalkyl, unsubstituted cycloalkyl, substituted heterocycloalkyl, unsubstituted heterocycloalkyl, alkoxy, substituted alkylamino, unsubstituted alkylamino, substituted alkylthio, unsubstituted alkylthio, alkyl group substituted by a carboxy, a sulfo, a phosphate, —(CH$_2$)$_a$—[O—(CH$_b$)]$_m$—O—Z, where Z is H, alkyl, carboxy, sulfo, phosphate; each of a and b is an integer from 1 to 4; m is an integer selected from 1 to 12;

n is 0, 1, or 2;

ψ– is a biologically compatible counterion.

In some embodiments, the dyes used for the invention are dimers of substituted unsymmetric cyanine dyes with a hydrophilic bridge to improve water soluability and stability. These dyes may have at least one feature, or all of the following features: relatively low "fluorescence background" (fluorescence in the absence of nucleic acids), if any, and ideally, no fluorescence background; relative low toxicity, and ideally, no toxicity; relatively high fluorescent signalstrength; and relative high water soluability and stability in water. These dyes are preferably better as to at least one of these features than existing dyes, such as Ethidium Bromide, SYBR Green I, SYBR Gold, and SYBR Safe. The substituted unsymmetric cyanine dye units are linked by a bridge between the cyanine dye units. The two dye units, which may be the same or different, may be bridged symmetrically or asymmetrically. The novel dimers generally have the formula:

substituted by a phosphate, —(CH$_2$)$_a$—[O—(CH$_b$)]$_o$—O—Z, where Y is absent, O, NH(C=O), C(=O)NH, or S(=O)$_2$NH; Z is H, alkyl, carboxy, sulfo, phosphate; each of a and b is an integer from 1 to 4; o is an integer selected from 1 to 12;

Each of t and s is an integer from 0 to 4;

Each of R$^2$ and R$^7$ is independently a substituted alkyl, unsubstituted alkyl, substituted arylalkyl, unsubstituted arylalkyl, substituted heteroalkyl, unsubstituted heteroalkyl, alkoxy, alkyl group substituted by a carboxy, a sulfo, a phosphate, a alkylamino, a dialkylamino, a alkylaminocarbonyl, a dialkylaminocarbonyl, a alkylaminosulfonamide, a dialkylaminosulfonamide, —(CH$_2$)$_a$—[O—(CH$_b$)]$_o$—O—Z, where Z is H, alkyl, carboxy, sulfo, phosphate; each of a and b is an integer from 1 to 4; o is an integer selected from 1 to 12; Each of R$^3$ and R$^6$ is independently H, substituted aryl, or unsubstituted aryl; Each of R$^4$ and R$^5$ is independently H, substituted alkyl, unsubstituted alkyl, substituted heteroalkyl, unsubstituted heteroalkyl, substituted arylalkyl, unsubstituted arylalkyl, substituted aryl, unsubstituted aryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio;

n and m, which may be the same or different, is 0, 1, or 2;

ψ– is a biologically compatible counterion;

-BRIDGE- has the general formula:

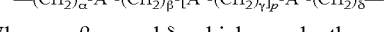

—(CH$_2$)$_\alpha$-A$^1$-(CH$_2$)$_\beta$-[A$^2$-(CH$_2$)$_\gamma$]$_p$-A$^3$-(CH$_2$)$_\delta$—

Where α, β, γ, and δ, which may be the same or different, are integers from 1 to 12; p is integer from 1 to 24; A$^1$, A$^2$ and A$^3$, which may be the same or different, are independently O, S, CH$_2$, NR$^{12}$, where R$^{12}$ is H or an alkyl group having 1-4 carbons, N$^+$R$^{13}$R$^{14}$, where R$^{13}$ and R$^{14}$, which may be the same or different, are independently hydrogen or alkyl group having 1-4 carbons, C(=O)NR$^{15}$, where R$^{15}$ is H or an alkyl group having 1-4 carbons, or triazole.

In some embodiments, the dyes used for the invention are trimers of substituted unsymmetric cyanine dyes with a hydrophilic bridge to improve water soluability and stability. These dyes may have at least one feature, or all of the following features: relatively low "fluorescence background" (fluorescence in the absence of nucleic acids), if any, and ideally,

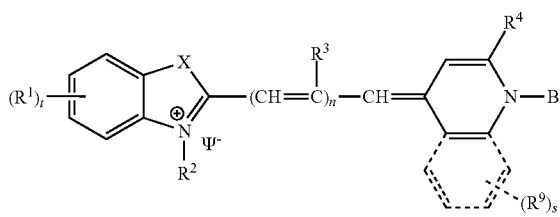

wherein:

X is O, S, C(CH$_3$)$_2$;

Each of R$^1$, R$^8$, R$^9$ and R$^{10}$ is independently hydrogen, carboxy, sulfo, phosphate, phosphonate, hydroxyl, halogen, CN, amino, alkylamino, dialkylamino, alkoxy, alkyl, substituted alkyl, aryl, heteroaryl, alkylaminocarbonyl, dialkylaminocarbonyl, alkylaminosulfonamide, dialkylaminosulfonamide, alkyl group substituted by a carboxy, alkyl group substituted by a sulfo, alkyl group no fluorescence background; relative low toxicity, and ideally, no toxicity; relatively high fluorescent signalstrength; and relative high water soluability and stability in water. These dyes are preferably better as to at least one of these features than existing dyes, such as Ethidium Bromide, SYBR Green I, SYBR Gold, and SYBR Safe. The substituted unsymmetric cyanine dye units are linked by a bridge between the cyanine dye units. The novel trimers generally have the formula:

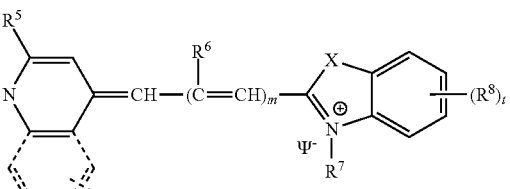

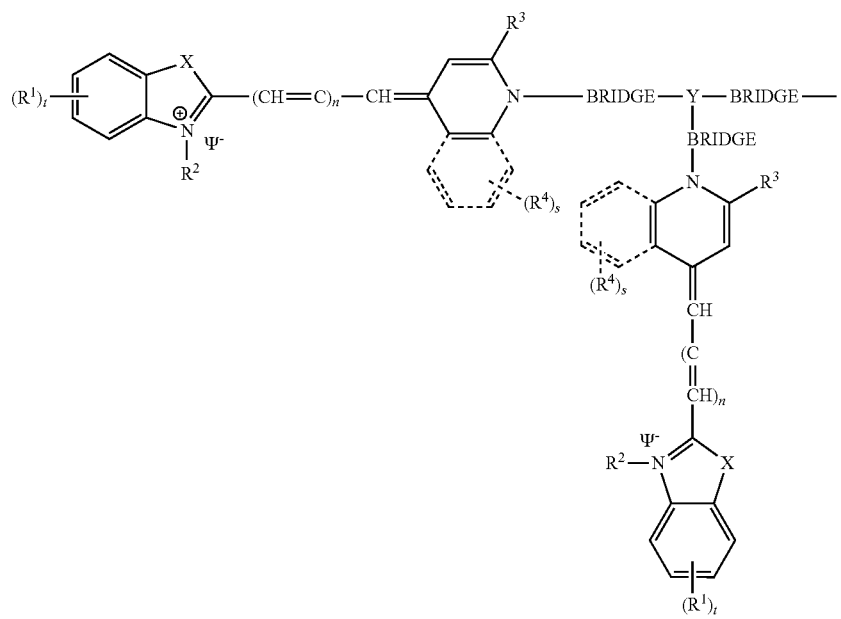

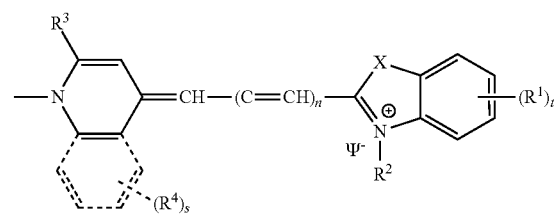

wherein:

X is O, S, C(CH$_3$)$_2$;

Each of R$^1$ and R$^4$ is independently hydrogen, carboxy, sulfo, phosphate, phosphonate, hydroxyl, halogen, CN, amino, alkylamino, dialkylamino, alkoxy, alkyl, aryl, heteroaryl, alkylaminocarbonyl, alkylaminosulfonamide;

Each of t and s is an integer from 0 to 4;

R$^2$ is a substituted alkyl, unsubstituted alkyl, substituted arylalkyl, unsubstituted arylalkyl, substituted heteroalkyl, unsubstituted heteroalkyl, alkoxy, alkyl group substituted by a carboxy, a sulfo, a phosphate, a alkylamino, a dialkylamino, a alkylaminocarbonyl, a dialkylaminocarbonyl, a alkylaminosulfonamide, a dialkylaminosulfonamide;

R$^3$ is H, substituted alkyl, unsubstituted alkyl, substituted heteroalkyl, unsubstituted heteroalkyl, substituted arylalkyl, unsubstituted arylalkyl, substituted aryl, unsubstituted aryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio;

n is 0, 1, or 2;

ψ– is a biologically compatible counterion;

-BRIDGE- has the general formula:

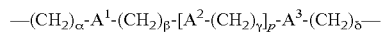

Where α, β, γ, and δ, which may be the same or different, are integers from 1 to 6; p is integer from 1 to 12; A$^1$, A$^2$ and A$^3$, which may be the same or different, are independently O, S, CH$_2$, NR$^{12}$, where R$^{12}$ is H or an alkyl group having 1-4 carbons, N$^+$R$^{13}$R$^{14}$, where R$^{13}$ and R$^{14}$, which may be the same or different, are independently hydrogen or alkyl group having 1-4 carbons, C(=O)NR$^{15}$, where R$^{15}$ is H or an alkyl group having 1-4 carbons, or triazole;

Y is a scaffold.

In some embodiments, the dyes used for the invention are tetraimers of substituted unsymmetric cyanine dyes with a hydrophilic bridge to improve water soluability and stability. These dyes may have at least one feature, or all of the following features: relatively low "fluorescence background" (fluorescence in the absence of nucleic acids), if any, and ideally, no fluorescence background; relative low toxicity, and ideally, no toxicity; relatively high fluorescent signalstrength; and relative high water soluability and stability in water. These dyes are preferably better as to at least one of these features than existing dyes, such as Ethidium Bromide, SYBR Green I, SYBR Gold, and SYBR Safe. The substituted unsymmetric cyanine dye units are linked by a bridge between the cyanine dye units. The novel tetramers generally have the formula:

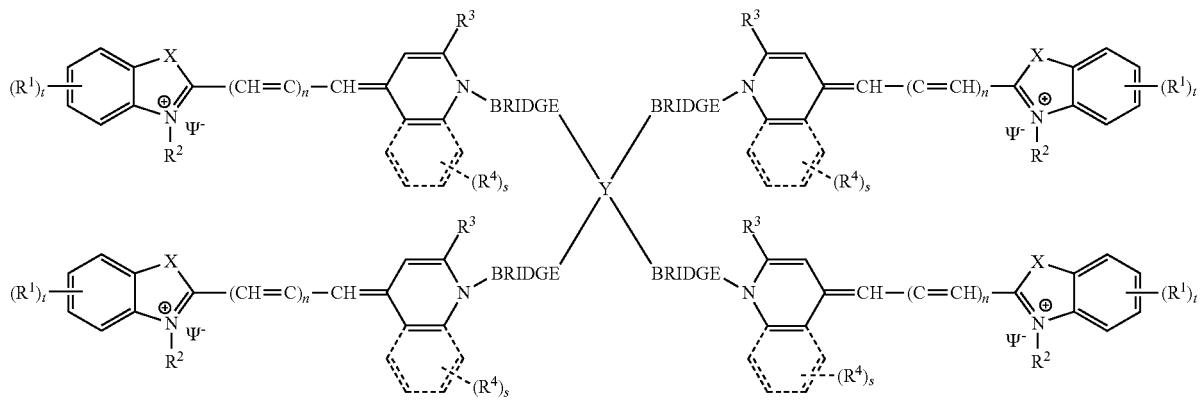

wherein:

X is O, S, C(CH$_3$)$_2$;

Each of R$^1$ and R$^4$ is independently hydrogen, carboxy, sulfo, phosphate, phosphonate, hydroxyl, halogen, CN, amino, alkylamino, dialkylamino, alkoxy, alkyl, aryl, heteroaryl, alkylaminocarbonyl, alkylaminosulfonamide;

Each of t and s is an integer from 0 to 4;

R$^2$ is a substituted alkyl, unsubstituted alkyl, substituted arylalkyl, unsubstituted arylalkyl, substituted heteroalkyl, unsubstituted heteroalkyl, alkoxy, alkyl group substituted by a carboxy, a sulfo, a phosphate, a alkylamino, a dialkylamino, a alkylaminocarbonyl, a dialkylaminocarbonyl, a alkylaminosulfonamide, a dialkylaminosulfonamide;

R$^3$ is H, substituted alkyl, unsubstituted alkyl, substituted heteroalkyl, unsubstituted heteroalkyl, substituted arylalkyl, unsubstituted arylalkyl, substituted aryl, unsubstituted aryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio;

n is 0, 1, or 2;

ψ− is a biologically compatible counterion;

-BRIDGE- has the general formula:

—(CH$_2$)$_\alpha$-A$^1$-(CH$_2$)$_\beta$-[A$^2$(CH$_2$)$_\gamma$]$_p$-A$^3$-(CH$_2$)$_\delta$—

Where α, β, γ, and δ, which may be the same or different, are integers from 1 to 6; p is integer from 1 to 12; A$^1$, A$^2$ and A$^3$, which may be the same or different, are independently O, S, CH$_2$, NR$^{12}$, where R$^{12}$ is H or an alkyl group having 1-4 carbons, N$^+$R$^{13}$R$^{14}$, where R$^{13}$ and R$^{14}$, which may be the same or different, are independently hydrogen or alkyl group having 1-4 carbons, C(=O)NR$^{15}$, where R$^{15}$ is H or an alkyl group having 1-4 carbons, or triazole;

Y is a scaffold.

In some embodiments, a method of detection and quantitation of nucleic acids in a sample is provided. The detection method can be performed in solution, in electrophoretic gels and blots, in microarray, in dead or fixed cells, or in live cells. The method comprises exposing the sample to a fluorescent nucleic acid dye having the formula:

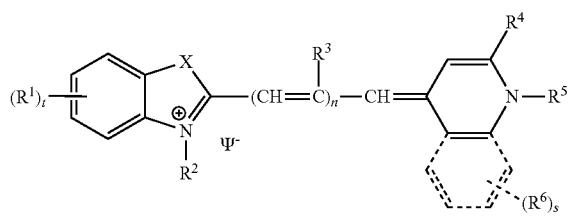

Or the formula:

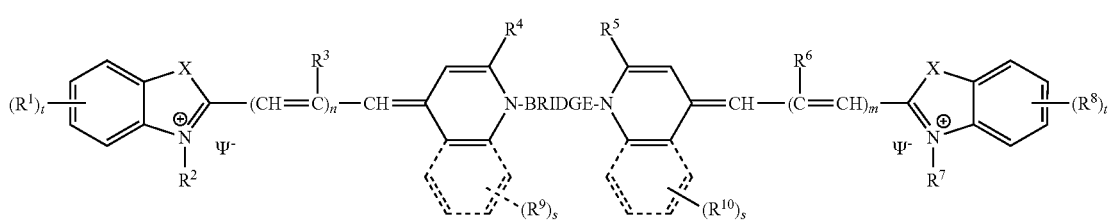

Or the formula:

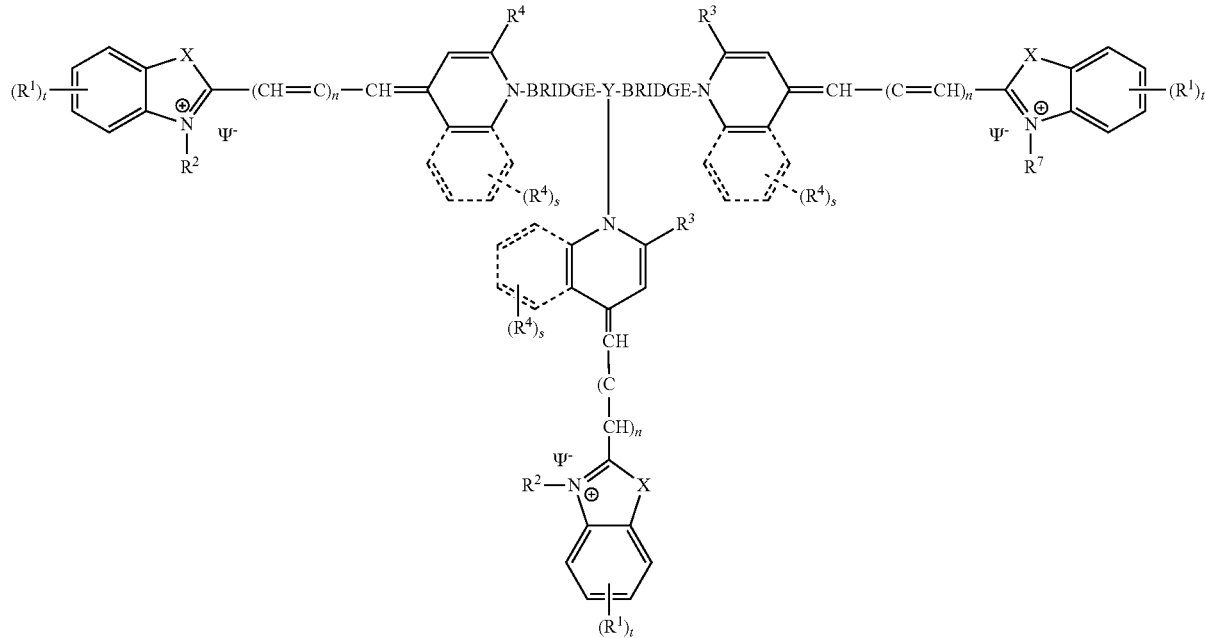

Or the formula:

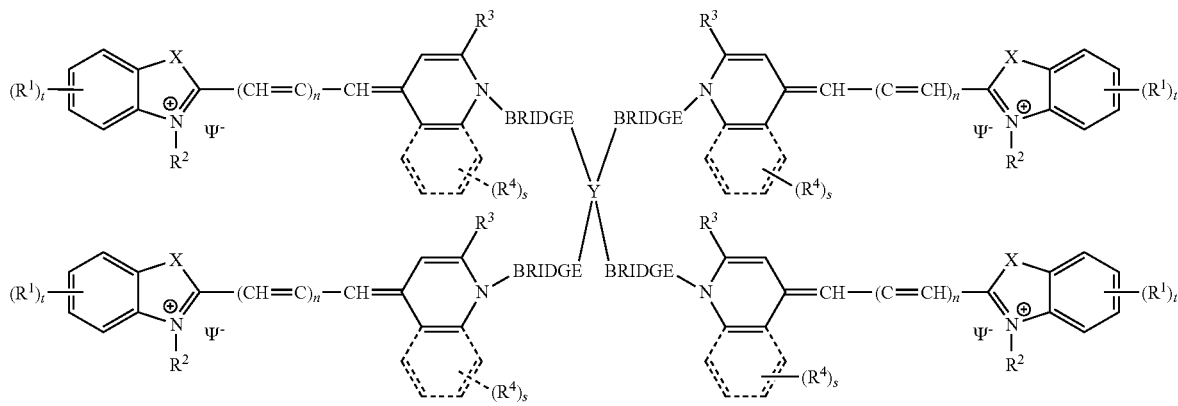

The substitute groups are the same as above-described.

In some embodiments, a kit of detection and quantitation of nucleic acids in a sample is provided. The kit comprises the fluorescent nucleic acid dye just described above, and information concerning use of the fluorescent nucleic acid dye. The kit may comprise, optionally, a buffer, a nucleic acid standard, or gel matrix. The fluorescent nucleic acid dye may be in an organic or aqueous solution, or in a gel matrix, such as a agarose gel matrix, for example.

BRIEF DESCRIPTION OF FIGURES

FIG. 1 shows a graphical representation of normalized fluorescence of compound 39 in the presence of DNA in TBE buffer and normalized fluorescence of SYBR Gold in the presence of DNA in TBE buffer, over time (days) at room temperature.

FIG. 2 shows a graphical representation of fluorescence emission spectra of compound 36, compound 40, and compound 49 in the presence of dsDNA, ssDNA, and RNA in TE buffer, respectively.

FIG. 3 shows a graphical representation of relative fluorescence versus DNA or RNA concentration in solution in the presence of compound 36 or compound 49, respectively.

FIG. 4 shows a graphical representation of gel upon post-DNA gel staining with compound 39, compound 65, and SYBR Safe, respectively.

FIG. 5 shows a graphical representation of cell imagings after incubation with compound 38, compound 42, and compound 61, in live cells and fixed cells, respectively.

DETAILED DESCRIPTION

Fluorescent dyes or stains are useful in various biological applications, such as nucleic acid detection, for example.

Methods associated with fluorescent dyes or stains, such as methods of use thereof, for example, are also useful. The substituted unsymmetrical cyanine dyes or dimers of the invention are virtually non-fluorescent when diluted in aqueous solution. When bound to nucleic acids, such as DNA or RNA, for example, becomes extremely fluorescent upon illumination. The dyes of the present invention can label nucleic acids in a wide variety of samples, particular in aqueous solutions, electrophoretic gels and blots, microarray, and a wide variety of cells, including microorganisms.

The section headings used herein are for organizational purposes only and are not to be construed as limiting the subject matter described.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

In this application, the use of "or" means "and/or" unless stated otherwise. In the context of a multiple dependent claim, the use of "or" refers back to more than one preceding independent or dependent claim in the alternative only.

As utilized in accordance with the present disclosure, the following terms, unless otherwise indicated, shall be understood to have the following meanings:

The terms "stain" and "dye" may be used interchangeably, and refer to an aromatic molecule capable of absorbing light in the spectral range of from about 250 nm to about 1000 nm, inclusive. The term "dye" may refer to a fluorescent dye, a non-fluorescent dye, or both. The term "fluorescent dye" refers to a dye capable of emitting light when excited by another light of appropriate wavelength.

The terms "nucleic acid" refers to double-stranded DNA (dsDNA), single-stranded DNA (ssDNA), double-stranded RNA (dsRNA), single-stranded RNA (ssRNA), and/or derivatives thereof. A nucleic acid may be natural or synthetic.

The terms "fluorescent nucleic acid stain" or "fluorescent nucleic acid dye" refers to a dye capable of binding to a nucleic acid to form a fluorescent dye-nucleic acid complex. A fluorescent nucleic acid dye is typically non-fluorescent or weakly fluorescent by itself, but becomes highly fluorescent upon nucleic acid binding. The term "fluorescent DNA dye" refers to a dye that becomes fluorescent upon binding to DNA.

The term "TE" refers to an aqueous buffer comprising about 10 mM Tris and about 1 mM EDTA. The term "TBE" refers to an aqueous buffer comprising about 89 mM Tris, about 89 mM borate, and about 2 mM EDTA, with a pH of about 8.3 The term "TAE" refers to an aqueous buffer comprising about 40 mM Tris, about 20 mM acetate, and about 2 mM EDTA, with a pH of about 8.1.

In some embodiments, the substituted unsymmetrical cyanine dyes of the invention comprise: 1) a first heterocyclic ring system that is a substituted benzazolium ring, the ring system is optionally further substituted by a variety of substituents; 2) a bridging methine; and 3) a second heterocyclic ring that is a pyridinium or quinolinium ring system, one or more positions of which may be substituted by substituents. The dye structures generally have the formula:

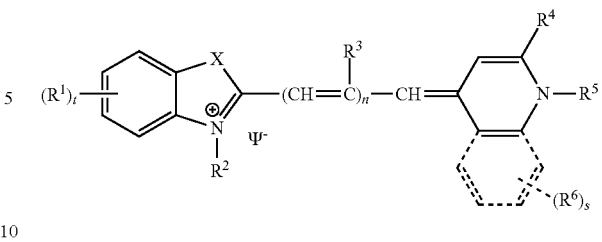

The double bond in the center can be in either cis or trans configuration. Mixtures of both configurations are also possible in a simple of a particular compound.

The value n can be 0, 1, or 2. When n=0 the dyes are unsymmetrical monomethine dyes; when n=1 the dyes are trimethine dyes; when n=2 the dyes are pentamethine dyes. It has been recognized from studies involving similar compounds that the number of methane groups between the heteroaromatic rings has a considerable influence on the spectral properties of the dye (Griffiths, COLOUR AND CONSTITUTION OF ORGANIC MOLECULES, pp. 241, Academic Press (1976)).

X can be one of O, S, or $C(CH_3)_2$. In preferred embodiments, X is O, or S.

Groups $R^1$ and $R^6$ can independently comprise or be hydrogen, carboxy, sulfo, phosphate, phosphonate, hydroxyl, halogen, CN, amino, alkylamino, substituted alkylamino, dialkylamino, alkoxy, alkyl, aryl, heteroaryl, alkylaminocarbonyl, dialkylaminocarbonyl, alkylaminosulfonamide, dialkylaminosulfonamide, alkyl group substituted by a carboxy, alkyl group substituted by a sulfo, alkyl group substituted by a phosphate, —Y—$(CH_2)_a$—[O—$(CH_2)_b]_m$—O—Z, where Y is absent, O, NH(C=O), C(=O)NH, or S(=O)$_2$NH; Z is H, alkyl, carboxy, sulfo, phosphate; each of a and b is an integer from 1 to 4; m is an integer selected from 1 to 12. Preferably the substitute $R^1$ is hydrogen, carboxy, sulfo. Preferably the substitute $R^6$ is methyl, or methoxyl.

The value t or s can be 0, 1, 2, 3 and 4. When the substituent group $R^1$ or $R^6$ is more than one substituent, the substituents may be the same or different. Typically, the compound contains no more than one $R^1$ or $R^6$ that is not H.

The substitute $R^2$ can be a substituted alkyl, unsubstituted alkyl, substituted arylalkyl, unsubstituted arylalkyl, substituted heteroalkyl, unsubstituted heteroalkyl, alkoxy, alkyl group substituted by a carboxy, a sulfo, a phosphate, an alkylamino, a dialkylamino, an alkylaminocarbonyl, a dialkylaminocarbonyl, an alkylaminosulfonamide, a dialkylaminosulfonamide, —$(CH_2)_a$[O—$(CH_2)_b]_m$—O—Z, where Z is H, alkyl, carboxy, sulfo, phosphate; each of a and b is an integer from 1 to 4; m is an integer selected from 1 to 24. Preferably the substitute $R^2$ is an alkyl group having 1-6 carbons, more preferably methyl.

The substitute $R^3$ can be H, substituted aryl, or unsubstituted aryl. Incorporation of a non-hydrogen substituent $R^3$ can be used to adjust the binding selectivity on DNA or RNA. For instance when $R^3$ is methyl 4-benzoate (compound 47), it has high selectivity for RNA over DNA; when $R^3$ is H (compound 53), it has high selectivity for DNA over RNA.

The substitute $R^4$ can be H, substituted alkyl, unsubstituted alkyl, substituted heteroalkyl, unsubstituted heteroalkyl, substituted arylalkyl, unsubstituted arylalkyl, substituted aryl, unsubstituted aryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio. Preferably the substitute $R^4$ is alkyl having 1-6 carbons, aryl, alkylamino, dialkylamino.

The substitute $R^5$ can be substituted alkyl, unsubstituted alkyl, substituted heteroalkyl, unsubstituted heteroalkyl, substituted arylalkyl, unsubstituted arylalkyl, substituted aryl, unsubstituted aryl, substituted cycloalkyl, unsubstituted cycloalkyl, substituted heterocycloalkyl, unsubstituted heterocycloalkyl, alkoxy, substituted alkylamino, unsubstituted alkylamino, substituted alkylthio, unsubstituted alkylthio, alkyl group substituted by a carboxy, a sulfo, a phosphate, —$(CH_2)_a$[O—$(CH_2)_b$]$_m$—O—Z, where Z is H, alkyl, carboxy, sulfo, phosphate; each of a and b is an integer from 1 to 4; m is an integer selected from 1 to 24. Preferably the substitute $R^5$ is alkyl having 1-6 carbons, aryl, —$(CH_2)_a$[O—$(CH_2)_b$]$_m$—O—Z, where Z is H, methyl; each of a and b is an integer from 2 to 3; m is an integer selected from 2 to 12.

The counterion ψ– is a biologically compatible ion that is stable and synthetically accessible. As used herein, a substance that is biologically compatible is not toxic as used, and does not have a substantially deleterious effect on biomolecules. Examples of ψ– include, among others, chloride, bromide, iodide, sulfate, phosphate, perchlorate, tetrafluoroborate, nitrate, and anions of aromatic or aliphatic carboxylic acids. Preferred ψ– counterions are chloride, iodide, sulfate, perchlorate.

In some embodiments, at least one of $R^1$, $R^2$, $R^5$ and $R^6$ comprises or is a water soluble group.

In some embodiments, at least one of $R^1$, $R^2$, $R^5$ and $R^6$ comprises or is carboxy, sulfo, phosphate, alkyl group substituted by a carboxy, alkyl group substituted by a sulfo, alkyl group substituted by a phosphate, —Y—$(CH_2)_a$—[O—$(CH_2)_b$]$_m$—O—Z, where Y is absent, O, NH(C=O), C(=O)NH, or S(=O)$_2$NH; Z is H, alkyl, carboxy, sulfo, phosphate; each of a and b is an integer from 1 to 4; m is an integer selected from 1 to 24.

In some embodiments, at least one of $R^1$, $R^2$, $R^5$ and $R^6$ comprises or is sulfo, alkyl group substituted by a sulfo, —Y—$(CH_2)_a$-[O—$(CH_2)_b$]$_m$—O—Z, where Y is absent, O, NH(C=O), C(=O)NH, or S(=O)$_2$NH; Z is H, alkyl, sulfo; each of a and b is an integer from 2 to 3; m is an integer selected from 1 to 12.

In some embodiments, $R^1$ is H or sulfo, $R^2$ is methyl or ethyl, $R^5$ is H or methoxyl, and $R^6$ is alkyl, phenyl, benzyl, or —$(CH_2)_a$—[O—$(CH_2)_b$]$_m$—O—Z, where Z is H, methyl, sulfo; each of a and b is an integer from 2 to 3; m is an integer selected from 1 to 6.

Certain nonlimiting exemplary substituted unsymmetrical cyanine dyes are shown in Tables 1.

TABLE 1

Nonlimiting exemplary substituted unsymmetrical cyanine dye structures

| Compound | Structure |
|---|---|
| 1 | 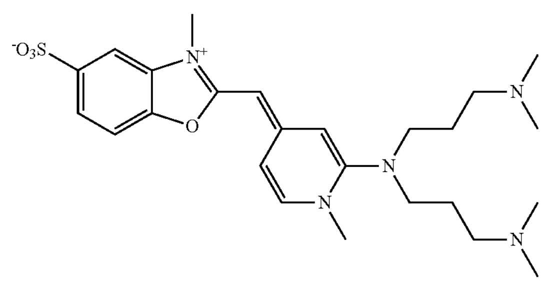 |
| 2 | 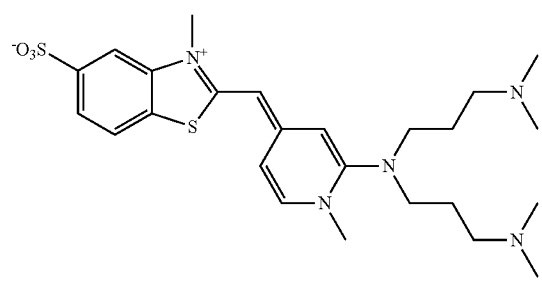 |
| 3 | 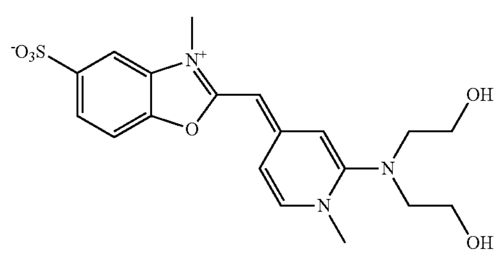 |

TABLE 1-continued

Nonlimiting exemplary substituted unsymmetrical cyanine dye structures

| Compound | Structure |
|---|---|
| 4 | 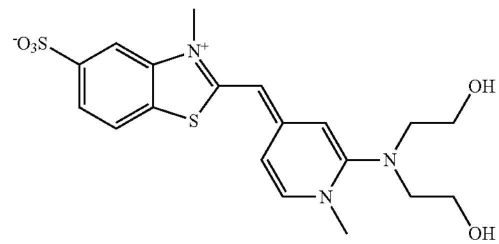 |
| 5 | 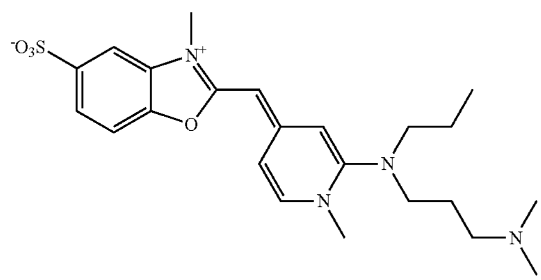 |
| 6 | 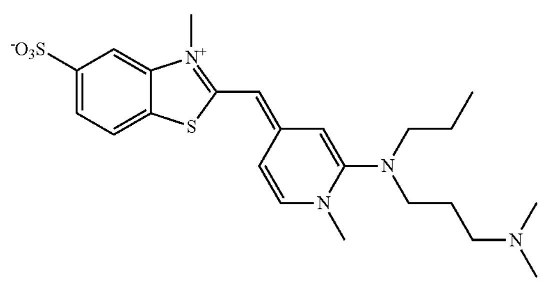 |
| 7 | 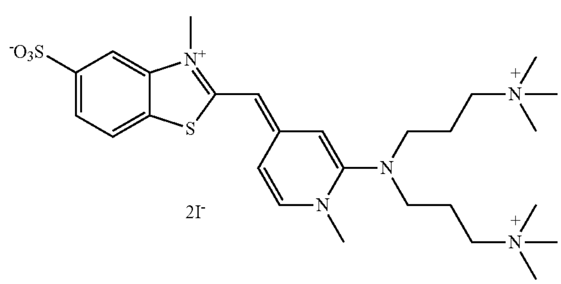 |
| 8 | 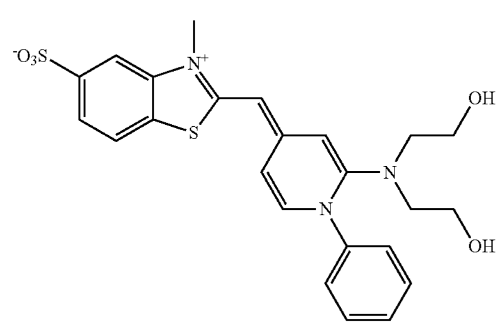 |

TABLE 1-continued
Nonlimiting exemplary substituted unsymmetrical cyanine dye structures
| Compound | Structure |
|---|---|
| 9 | 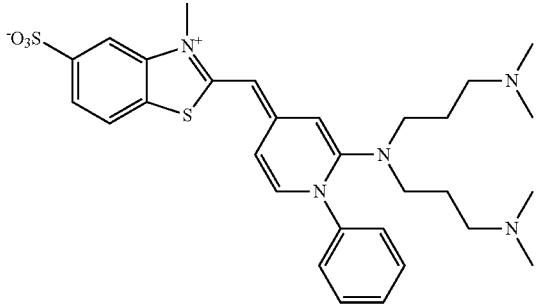 |
| 10 | 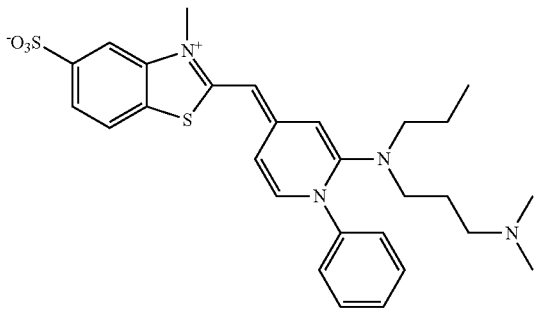 |
| 11 | 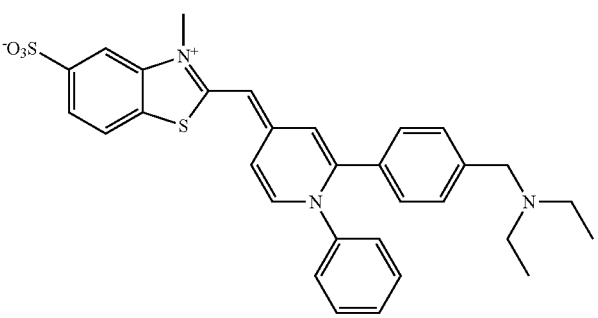 |
| 12 | 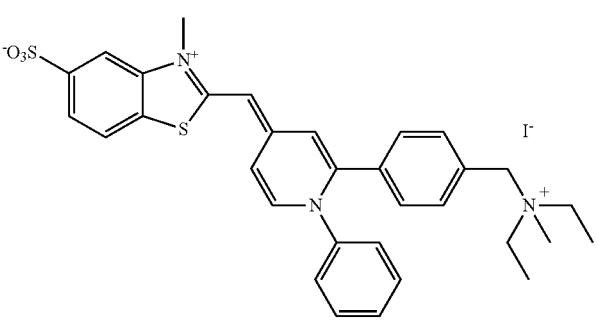 |

TABLE 1-continued
Nonlimiting exemplary substituted unsymmetrical cyanine dye structures
| Compound | Structure |
|---|---|
| 13 | 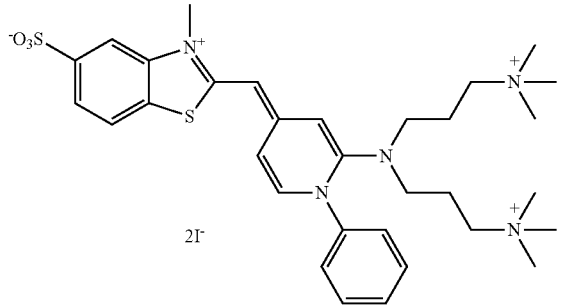 |
| 14 | 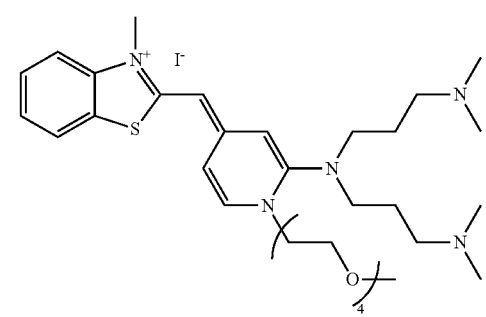 |
| 15 | 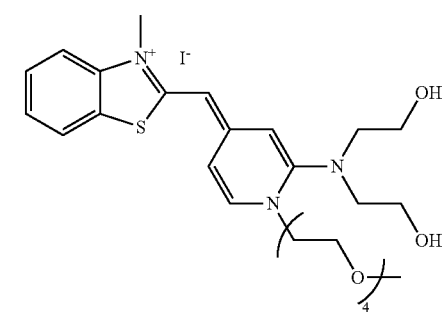 |
| 16 | 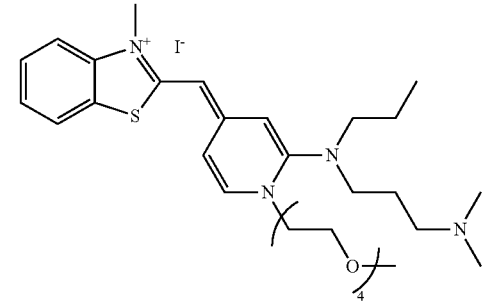 |

TABLE 1-continued

Nonlimiting exemplary substituted unsymmetrical cyanine dye structures

| Compound | Structure |
| --- | --- |
| 17 | 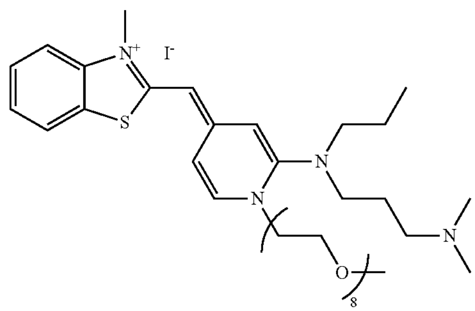 |
| 18 | 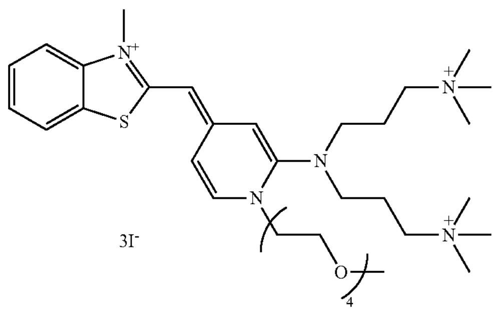 |
| 19 | 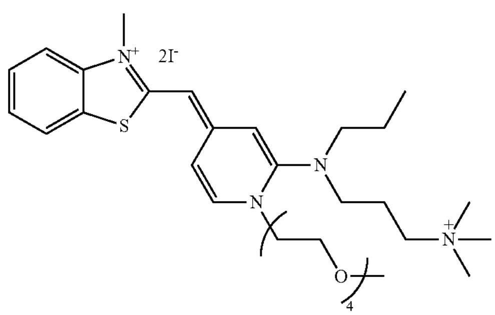 |
| 20 | 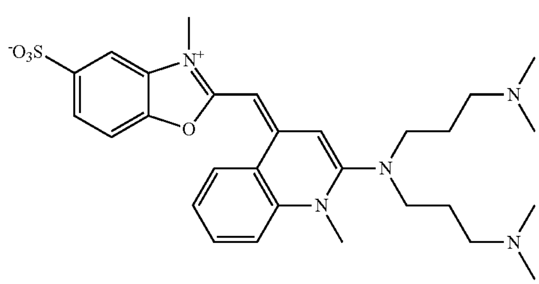 |
| 21 | 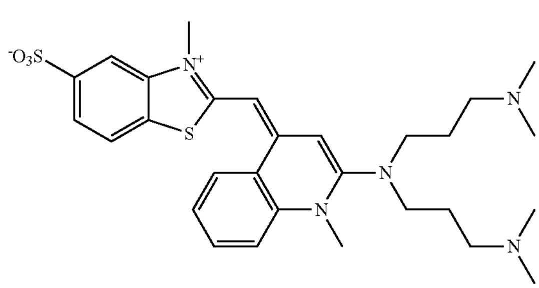 |

TABLE 1-continued

Nonlimiting exemplary substituted unsymmetrical cyanine dye structures

| Compound | Structure |
| --- | --- |
| 22 | 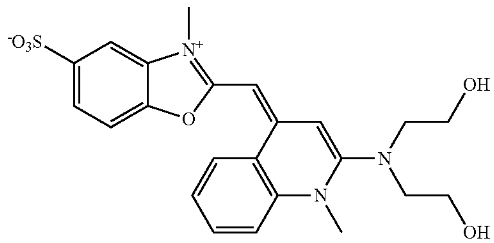 |
| 23 | 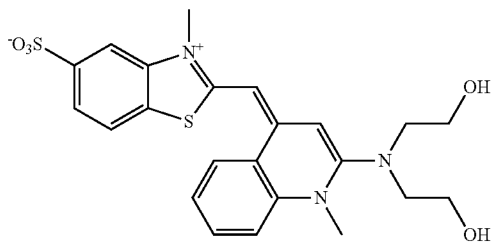 |
| 24 | 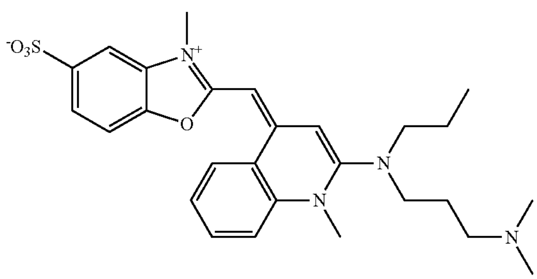 |
| 25 | 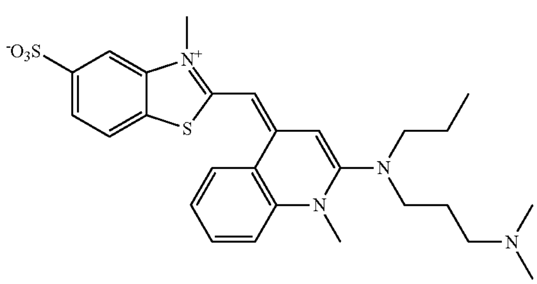 |
| 26 | 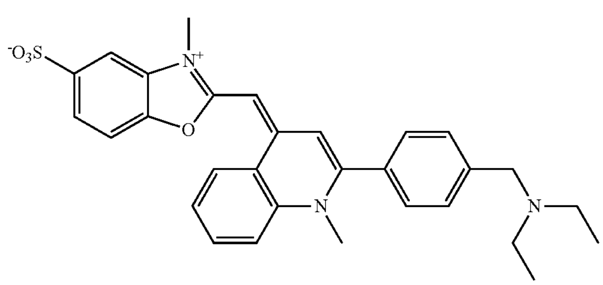 |

TABLE 1-continued

Nonlimiting exemplary substituted unsymmetrical cyanine dye structures

| Compound | Structure |
|---|---|
| 27 | 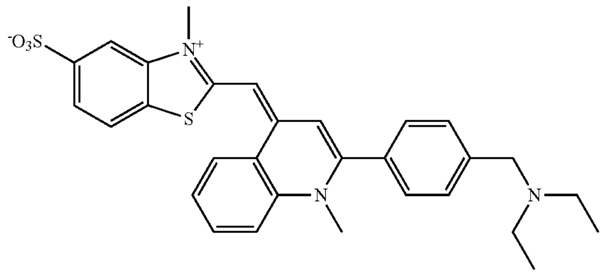 |
| 28 | 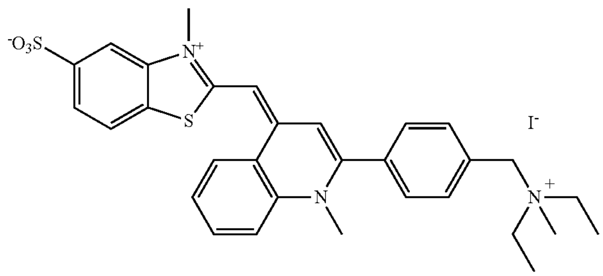 |
| 29 | 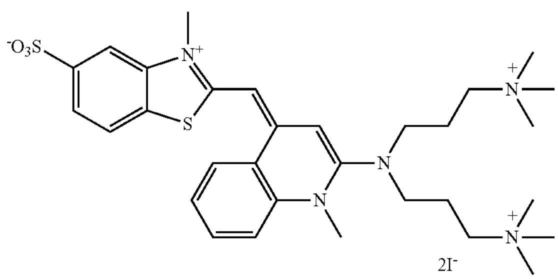 |
| 30 | 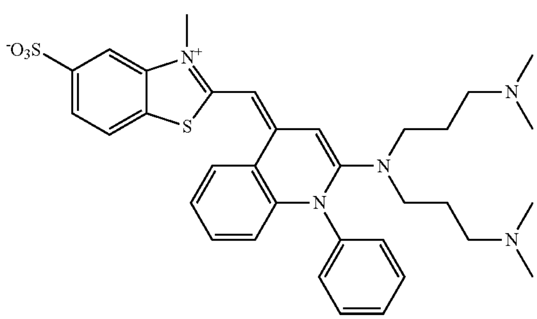 |
| 31 | 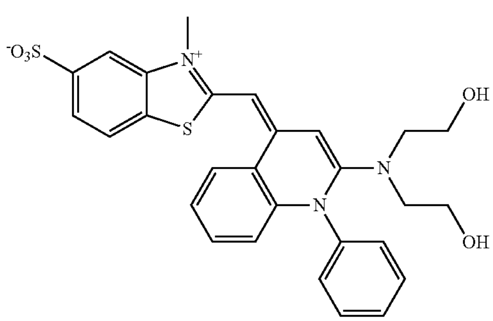 |

TABLE 1-continued

Nonlimiting exemplary substituted unsymmetrical cyanine dye structures

| Compound | Structure |
|---|---|
| 32 | 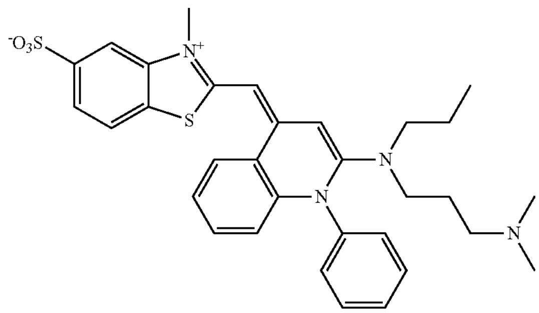 |
| 33 | 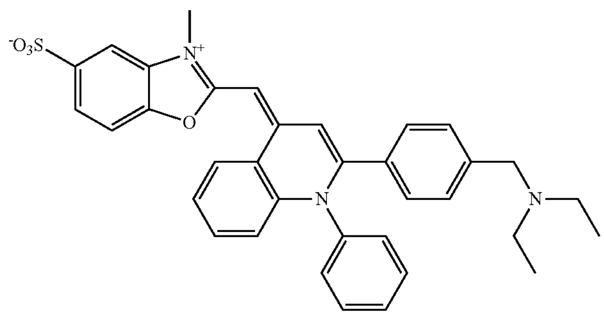 |
| 34 | 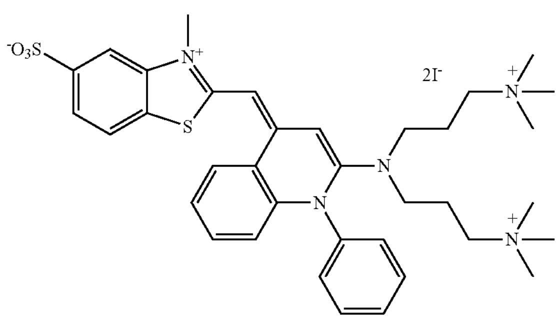 |
| 35 | 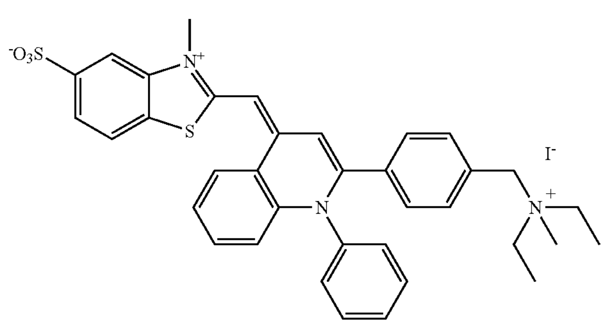 |

TABLE 1-continued

Nonlimiting exemplary substituted unsymmetrical cyanine dye structures

| Compound | Structure |
|---|---|
| 36 | 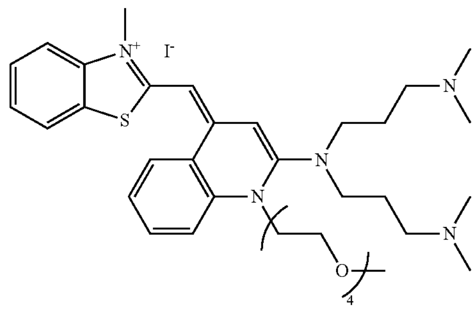 |
| 37 | 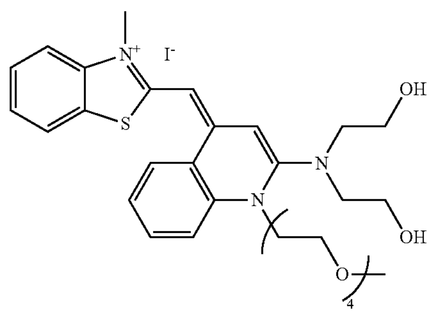 |
| 38 | 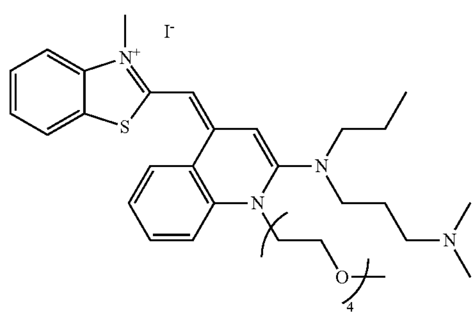 |
| 39 | 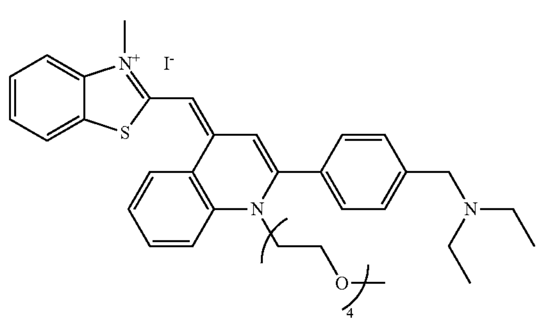 |

TABLE 1-continued
Nonlimiting exemplary substituted unsymmetrical cyanine dye structures
| Compound | Structure |
|---|---|
| 40 | 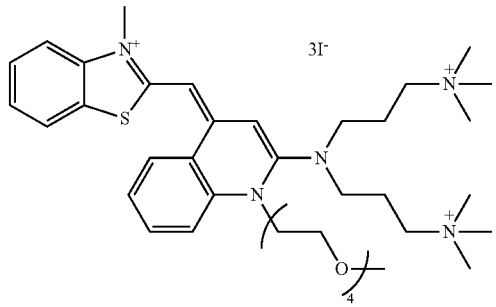 |
| 41 | 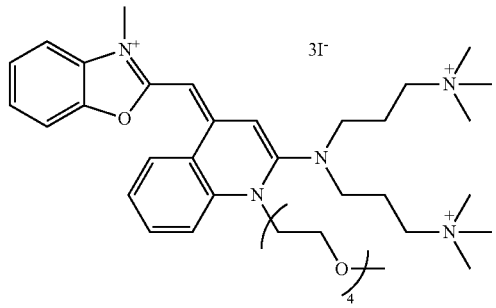 |
| 42 | 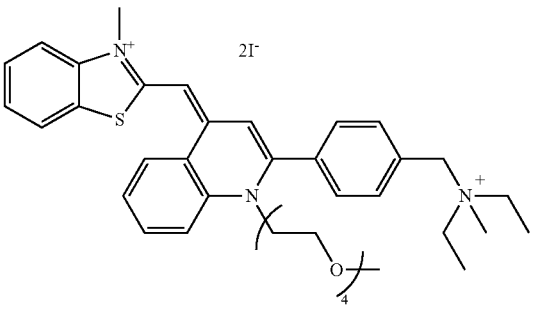 |
| 43 | 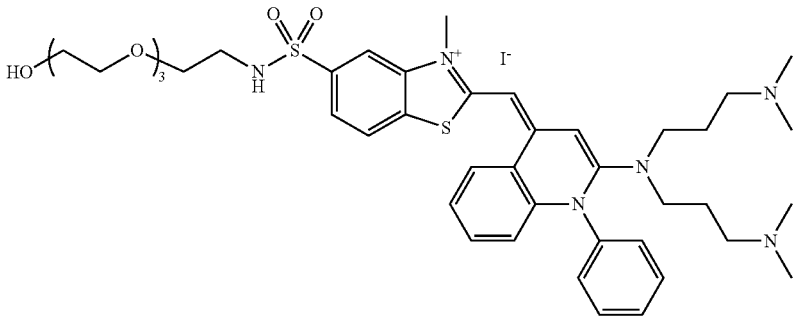 |

TABLE 1-continued

Nonlimiting exemplary substituted unsymmetrical cyanine dye structures

| Compound | Structure |
|---|---|
| 44 | 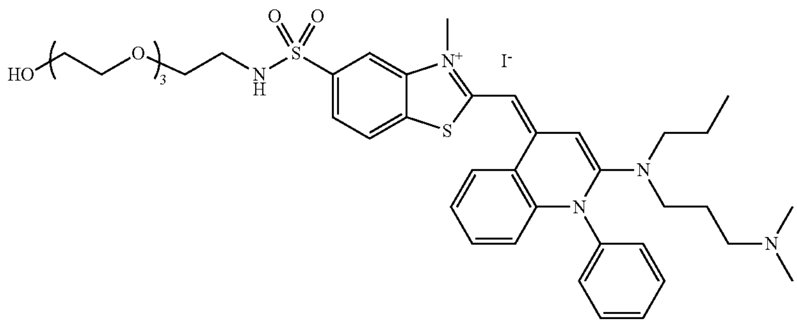 |
| 45 | 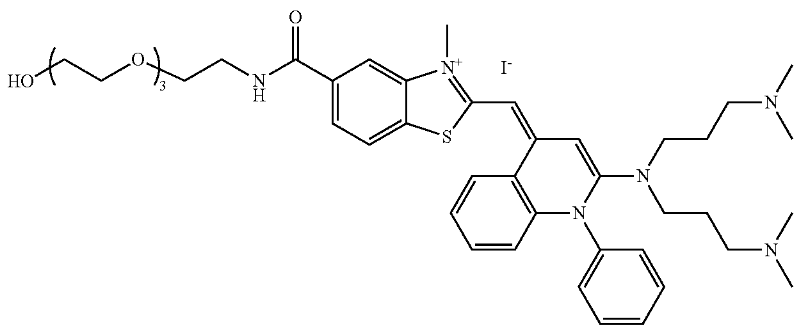 |
| 46 | 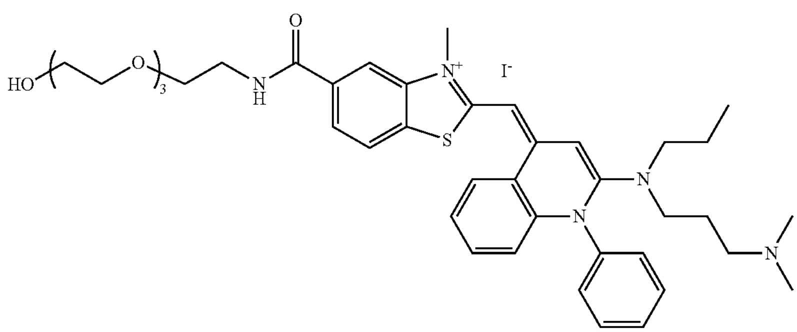 |
| 47 | 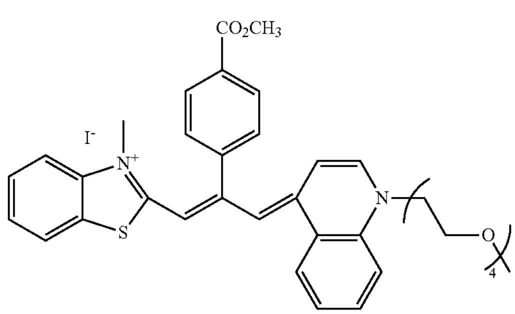 |

TABLE 1-continued
Nonlimiting exemplary substituted unsymmetrical cyanine dye structures
| Compound | Structure |
|---|---|
| 48 | 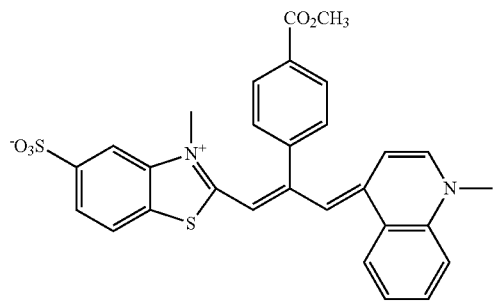 |
| 49 | 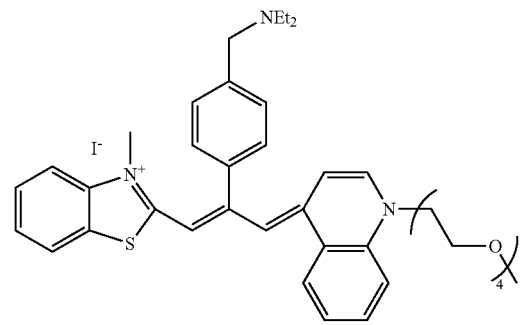 |
| 50 | 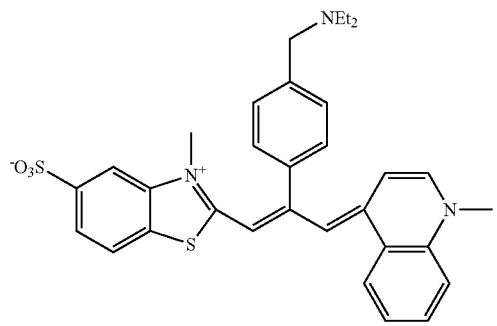 |
| 51 | 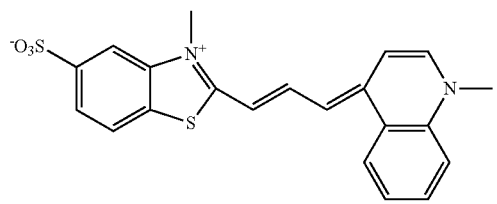 |
| 52 | 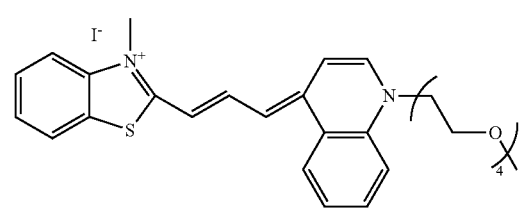 |

TABLE 1-continued

Nonlimiting exemplary substituted unsymmetrical cyanine dye structures

| Compound | Structure |
| --- | --- |
| 53 | 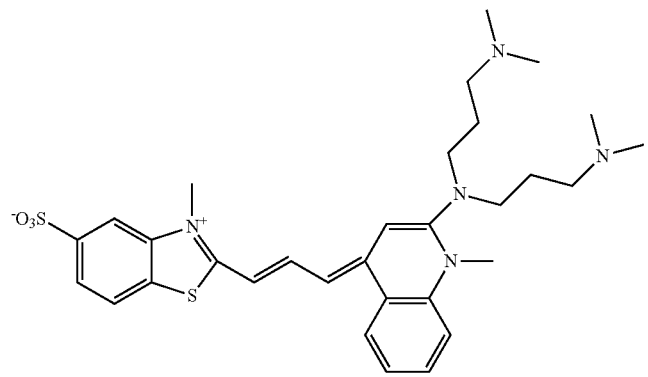 |
| 54 | 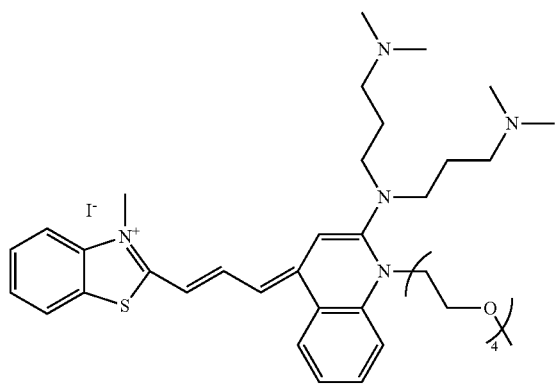 |

In some embodiments, the dimers of the substituted unsymmetrical cyanine dyes of the invention are linked by a bridge between two cyanine dye units. The two dye units, which may be the same or different, may be bridged symmetrically or asymmetrically. The dimer structures generally have the formula:

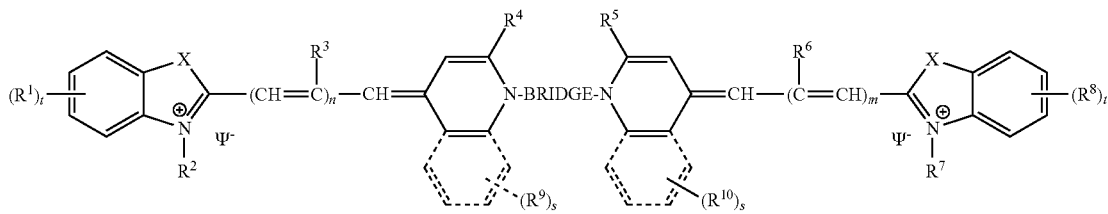

Groups $R^1$, $R^8$, $R^9$ and $R^{10}$ can independently comprise or be hydrogen, carboxy, sulfo, phosphate, phosphonate, hydroxyl, halogen, CN, amino, alkylamino, dialkylamino, alkoxy, alkyl, aryl, heteroaryl, alkylaminocarbonyl, dialkylaminocarbonyl, alkylaminosulfon-amide, dialkylaminosulfonamide, alkyl group substituted by a carboxy, alkyl group substituted by a sulfo, alkyl group substituted by a phosphate, —Y—$(CH_2)_a$—[O—$(CH_2)_b]_o$—O—Z, where Y is absent, O, NH(C=O), C(=O)NH, or S(=O)$_2$NH; Z is H, alkyl, carboxy, sulfo, phosphate; each of a and b is an integer from 1 to 4; o is an integer selected from 1 to 12. Preferably the substitutes $R^1$ and $R^8$ are hydrogen, carboxy, sulfo, or CN. Preferably the substitutes $R^9$ and $R^{10}$ is hydrogen, methyl, or methoxyl.

Groups $R^2$ and $R^7$ can independently comprise or be a substituted alkyl, unsubstituted alkyl, substituted arylalkyl, unsubstituted arylalkyl, substituted heteroalkyl, unsubstituted heteroalkyl, alkoxy, alkyl group substituted by a carboxy, a sulfo, a phosphate, an alkylamino, a dialkylamino, an alkylaminocarbonyl, a dialkylamino-carbonyl, an alkylaminosulfonamide, a dialkylaminosulfonamide, —$(CH_2)_a$-[O—$(CH_2)_b]_o$—O—Z, where Z is H, alkyl, carboxy, sulfo, phosphate; each of a and b is an integer from 1 to 4; o is an integer selected from 1 to 12. Preferably the substitutes $R^2$ and $R^7$ are alkyl containing 1-3 carbons. More preferably, $R^2$ and $R^7$ are methyl groups.

Groups $R^3$ and $R^6$ can independently comprise or be H, substituted aryl, or unsubstituted aryl. Preferably $R^3$ and $R^6$ are H.

Groups $R^4$ and $R^5$ can independently comprise or be H, substituted alkyl, unsubstituted alkyl, substituted heteroalkyl, unsubstituted heteroalkyl, substituted arylalkyl, unsubstituted arylalkyl, substituted aryl, unsubstituted aryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio. Preferably the substitutes $R^4$ and $R^5$ are alkyl having 1-6 carbons, aryl, alkylamino, dialkylamino.

X can be one of O, S, or $C(CH_3)_2$. In preferred embodiments, X is O, or S.

The subscripts n and m, which determine the length of each dye unit, are 0, 1, or 2. The dye units that form the dimer may be the same length or different. Changing the length of the dye units by increasing n or m or both will affect the spectral properties of the dye units and of the dimer.

The counterion ψ– is a biologically compatible ion that is stable and synthetically accessible. As used herein, a substance that is biologically compatible is not toxic as used, and does not have a substantially deleterious effect on biomolecules. Examples of ψ– include, among others, chloride, bromide, iodide, sulfate, phosphate, perchlorate, tetrafluoroborate, nitrate, and anions of aromatic or aliphatic carboxylic acids. Preferred ψ– counterions are chloride, iodide, sulfate, perchlorate.

The BRIDGE linking the two dye units, which may be charged or neutral, is a flexible linker molecule containing 4 to 40 non-hydrogen atoms. The linker contains at least one of heteroatoms N, O, or S, which may be the same or different.

-BRIDGE- has the general formula:

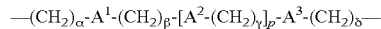

The subscripts α, β, γ, and δ, which may be the same or different, indicate the size of alkyl units, which contain from 1 to 12 carbon atoms each. The subscript p indicates the size of that unit, which may range from 1 to 12. $A^1$, $A^2$ and $A^3$, which may be the same or different, are independently O, S, $CH_2$, $NR^{12}$, where $R^{12}$ is H or an alkyl group having 1-6 carbons, $N^+R^{13}R^{14}$, where $R^{13}$ and $R^{14}$, which may be the same or different, are independently hydrogen or alkyl group having 1-6 carbons, $C(=O)NR^{15}$, where $R^{15}$ is H or an alkyl group having 1-6 carbons, or triazole. In a preferred embodiment, $A^1$ and $A^3$ are $NR^{12}$, $C(=O)NR^{15}$ or triazole, $A^2$ is O. More preferably, $R^{12}$ and $R^{15}$ are H.

Certain nonlimiting exemplary dimers of substituted unsymmetrical cyanine dye are shown in Tables 2.

TABLE 2

Nonlimiting exemplary dimer structures of substituted unsymmetrical cyanine dye

| Compound | Structure |
|---|---|
| 55 | 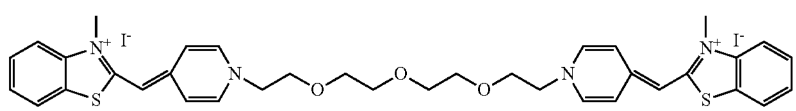 [SMILES: C[n+]1c(C=C2C=CN(CCOCCOCCOCCN3C=CC(=Cc4sc5ccccc5[n+]4C)C=C3)C=C2)sc2ccccc21 ; [I-] ; [I-]] |
| 56 | 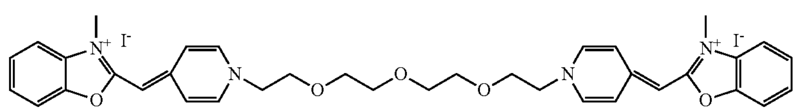 |
| 57 | 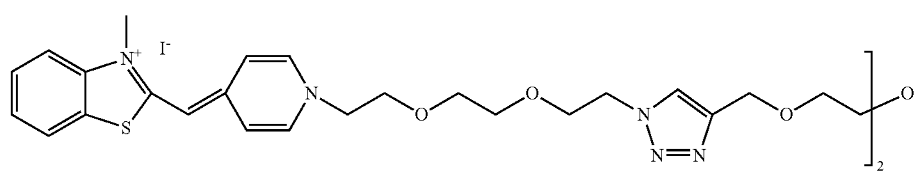 [SMILES: C[n+]1c(C=C2C=CN(CCOCCOCCn3cc(COCCO)nn3)C=C2)sc2ccccc21 ; [I-]] |
| 58 | 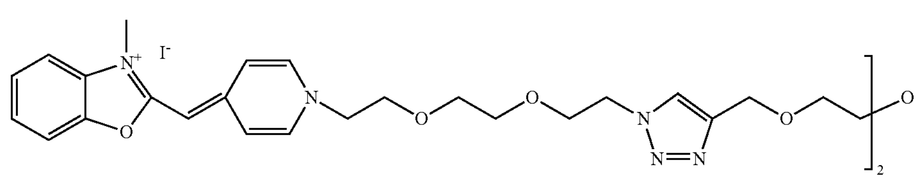 [SMILES: C[n+]1c(C=C2C=CN(CCOCCOCCn3cc(COCCO)nn3)C=C2)oc2ccccc21 ; [I-]] |
| 59 | 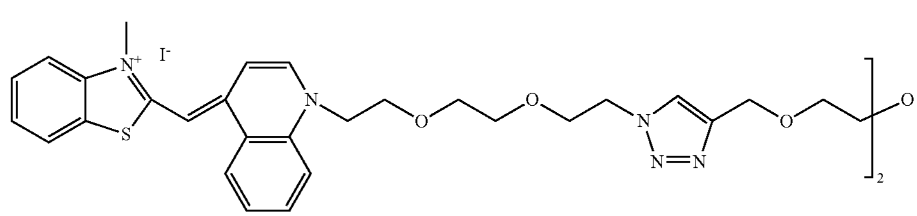 [SMILES: C[n+]1c(/C=C2\C=CN(CCOCCOCCn3cc(COCCO)nn3)c3ccccc32)sc2ccccc21 ; [I-]] |

TABLE 2-continued

Nonlimiting exemplary dimer structures of substituted unsymmetrical cyanine dye

| Compound | Structure |
|---|---|
| 60 | 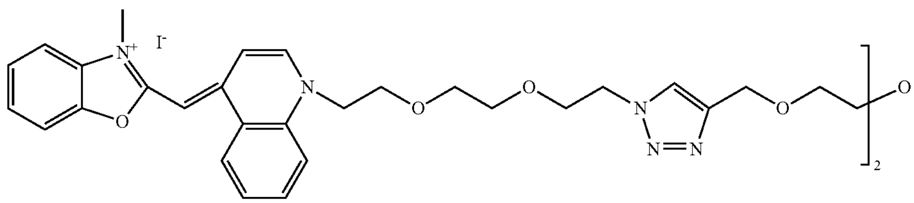 |
| 61 | 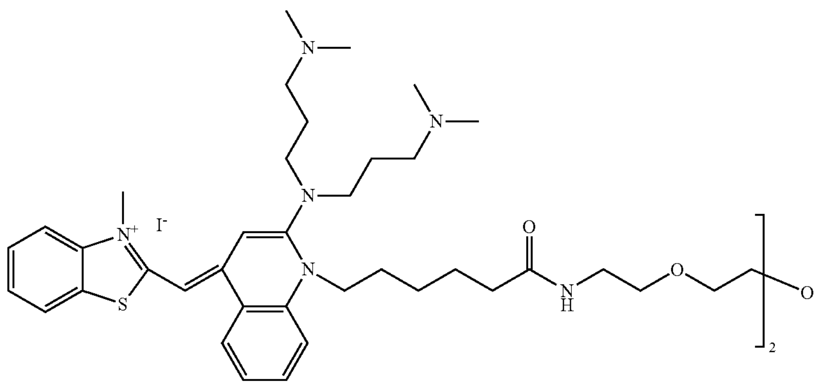 [SMILES: CN(C)CCCN(CCCN(C)C)C1=C/C(=C\c2sc3ccccc3[n+]2C)c2ccccc2N1CCCCCC(=O)NCCOCCO ; [I-]] |
| 62 | 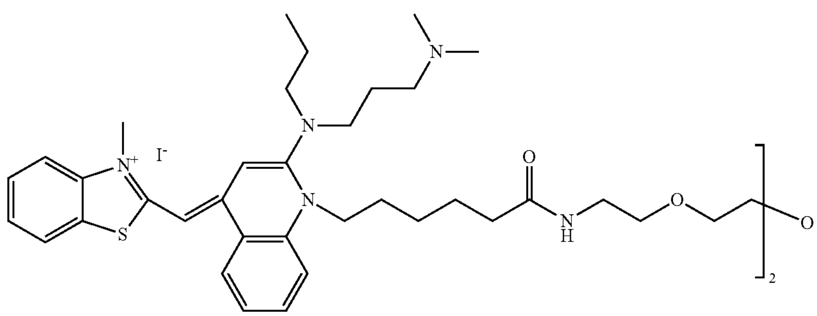 [SMILES: CCCN(CCCN(C)C)C1=C/C(=C\c2sc3ccccc3[n+]2C)c2ccccc2N1CCCCCC(=O)NCCOCCO ; [I-]] |
| 63 | 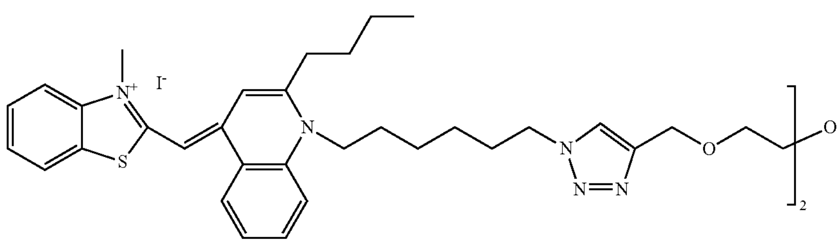 [SMILES: CCCCC1=C/C(=C\c2sc3ccccc3[n+]2C)c2ccccc2N1CCCCCCn1cc(COCCO)nn1 ; [I-]] |
| 64 | 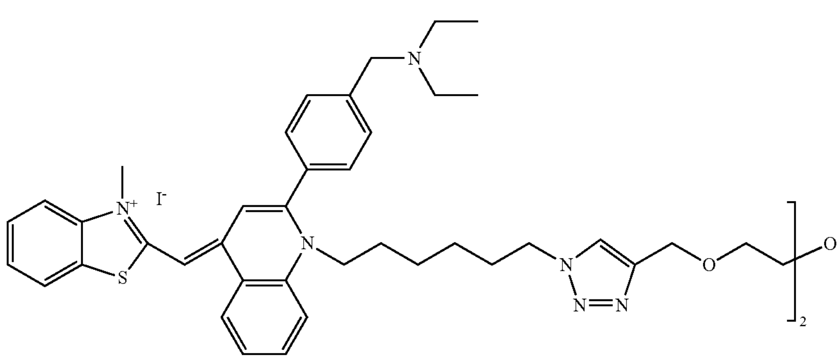 [SMILES: CCN(CC)Cc1ccc(C2=C/C(=C\c3sc4ccccc4[n+]3C)c3ccccc3N2CCCCCCn2cc(COCCO)nn2)cc1 ; [I-]] |

US 8,742,114 B2
43      44
TABLE 2-continued
Nonlimiting exemplary dimer structures of substituted unsymmetrical cyanine dye
| Compound | Structure |
|---|---|
| 65 | 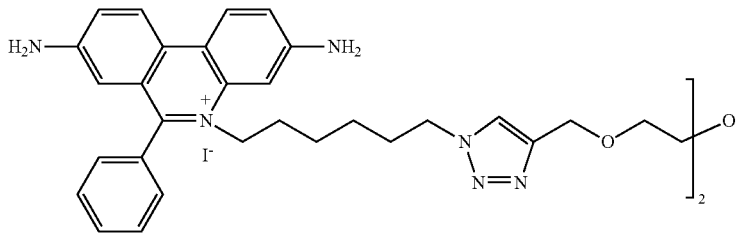 |
| 66 | 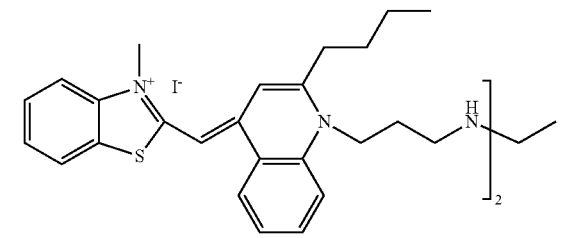 [SMILES: CCCCC1=C/C(=C\c2sc3ccccc3[n+]2C)c2ccccc2N1CCCNCC ; [I-]] |
| 67 | 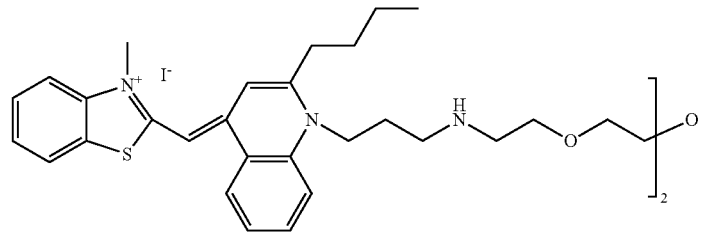 [SMILES: CCCCC1=C/C(=C\c2sc3ccccc3[n+]2C)c2ccccc2N1CCCNCCOCCO ; [I-]] |
| 68 | 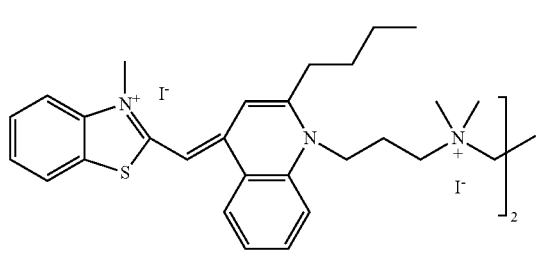 |
| 69 | 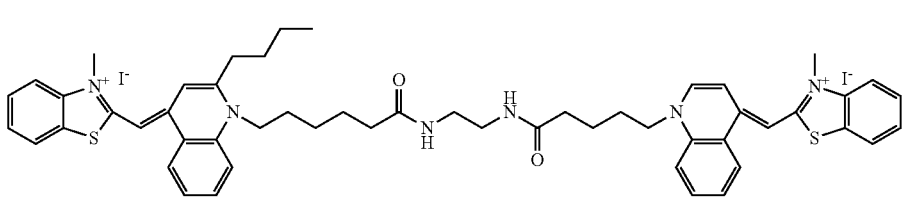 [SMILES: CCCCC1=C/C(=C\c2sc3ccccc3[n+]2C)c2ccccc2N1CCCCCC(=O)NCCNC(=O)CCCCN1C=C/C(=C\c2sc3ccccc3[n+]2C)c2ccccc21 ; [I-] ; [I-]] |

In some embodiments, the trimers of the substituted unsymmetrical cyanine dyes of the invention are linked by a bridge between three cyanine dye units. The trimer structures generally have the formula:

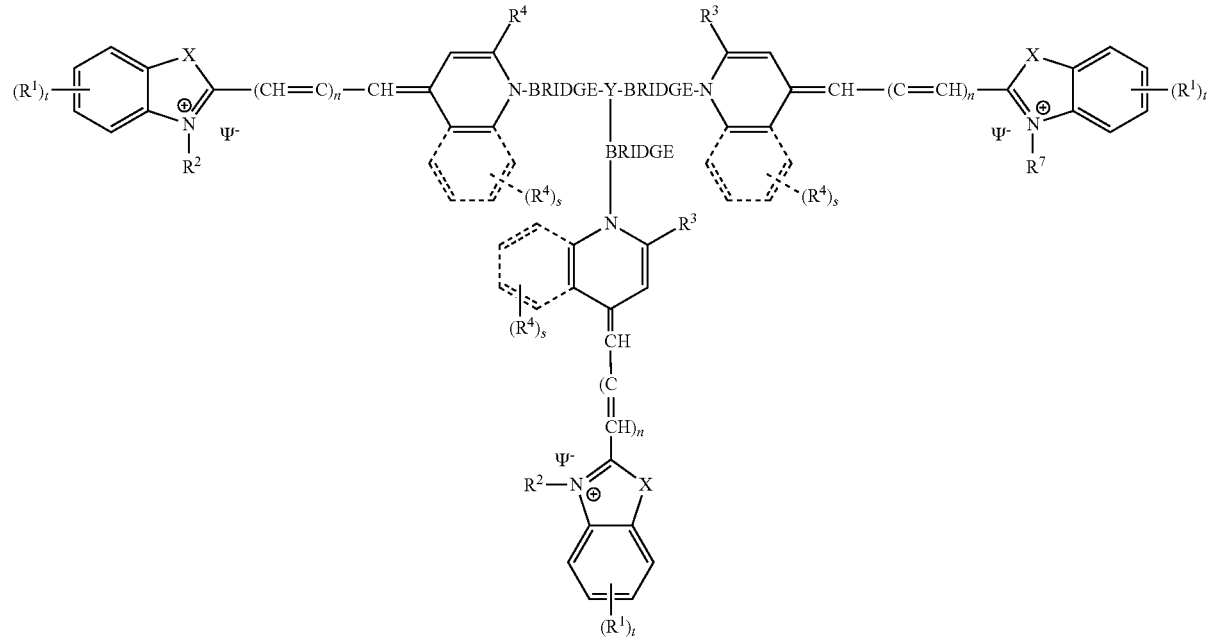

Groups $R^1$ and $R^4$ can independently comprise or be hydrogen, carboxy, sulfo, phosphate, phosphonate, hydroxyl, halogen, CN, amino, alkylamino, dialkylamino, alkoxy, alkyl, aryl, heteroaryl, alkylaminocarbonyl, dialkylaminocarbonyl, alkylaminosulfon-amide, dialkylaminosulfonamide, alkyl group substituted by a carboxy, alkyl group substituted by a sulfo, alkyl group substituted by a phosphate, —Y—$(CH_2)_a$—[O—$(CH_2)_b]_o$—O—Z, where Y is absent, O, NH(C=O), C(=O)NH, or S(=O)$_2$NH; Z is H, alkyl, carboxy, sulfo, phosphate; each of a and b is an integer from 1 to 4; o is an integer selected from 1 to 12. Preferably the substitutes $R^1$ is hydrogen, carboxy, sulfo, or CN. Preferably the substitutes $R^4$ is hydrogen, methyl, or methoxyl.

Groups $R^2$ can comprise or be a substituted alkyl, unsubstituted alkyl, substituted arylalkyl, unsubstituted arylalkyl, substituted heteroalkyl, unsubstituted heteroalkyl, alkoxy, alkyl group substituted by a carboxy, a sulfo, a phosphate, an alkylamino, a dialkylamino, an alkylaminocarbonyl, a dialkylamino-carbonyl, an alkylaminosulfonamide, a dialkylaminosulfonamide, —$(CH_2)_a$—[O—$(CH_2)_b]_o$—O—Z, where Z is H, alkyl, carboxy, sulfo, phosphate; each of a and b is an integer from 1 to 4; o is an integer selected from 1 to 12. Preferably the substitutes $R^2$ is alkyl containing 1-3 carbons. More preferably, $R^2$ is methyl groups.

Groups $R^3$ can comprise or be H, substituted alkyl, unsubstituted alkyl, substituted heteroalkyl, unsubstituted heteroalkyl, substituted arylalkyl, unsubstituted arylalkyl, substituted aryl, unsubstituted aryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio. Preferably the substitutes $R^3$ is alkyl having 1-6 carbons, aryl, alkylamino, dialkylamino.

X can be one of O, S, or C(CH$_3$)$_2$. In preferred embodiments, X is O, or S.

The subscripts n, which determine the length of each dye unit, are 0, 1, or 2. Changing the length of the dye units will affect the spectral properties of the dye units and of the trimer.

The counterion ψ– is a biologically compatible ion that is stable and synthetically accessible. As used herein, a substance that is biologically compatible is not toxic as used, and does not have a substantially deleterious effect on biomolecules. Examples of ψ– include, among others, chloride, bromide, iodide, sulfate, phosphate, perchlorate, tetrafluoroborate, nitrate, and anions of aromatic or aliphatic carboxylic acids. Preferred ψ– counterions are chloride, iodide, sulfate, perchlorate.

The BRIDGE linking the two dye units, which may be charged or neutral, is a flexible linker molecule containing 4 to 40 non-hydrogen atoms. The linker contains at least one of heteroatoms N, O, or S, which may be the same or different.

-BRIDGE- has the general formula:

$$-(CH_2)_\alpha-A^1-(CH_2)_\beta-[A^2-(CH_2)_\gamma]_p-A^3-(CH_2)_\delta-$$

The subscripts α, β, γ, and δ, which may be the same or different, indicate the size of alkyl units, which contain from 1 to 12 carbon atoms each. The subscript p indicates the size of that unit, which may range from 1 to 12. $A^1$, $A^2$ and $A^3$, which may be the same or different, are independently O, S, CH$_2$, NR$^{12}$, where R$^{12}$ is H or an alkyl group having 1-6 carbons, N$^+$R$^{13}$R$^{14}$, where R$^{13}$ and R$^{14}$, which may be the same or different, are independently hydrogen or alkyl group having 1-6 carbons, C(=O)NR$^{15}$, where R$^{15}$ is H or an alkyl group having 1-6 carbons, or triazole. In a preferred embodiment, $A^1$ and $A^3$ are NR$^{12}$, C(=O)NR$^{15}$ or triazole, $A^2$ is O. More preferably, R$^{12}$ and R$^{15}$ are H.

Y is a scaffold.

Certain nonlimiting exemplary trimers of substituted unsymmetrical cyanine dye are shown in Tables 3.

TABLE 3
Nonlimiting exemplary trimer structures of substituted unsymmetrical cyanine dye
| Compound | Structure |
| --- | --- |
| 70 | 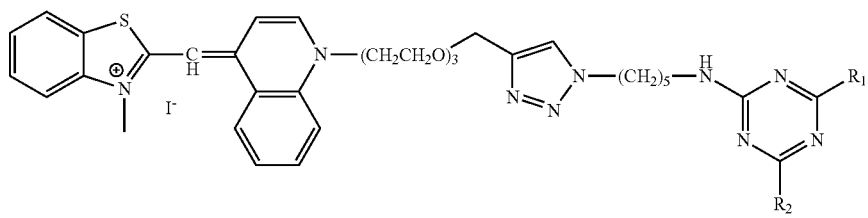 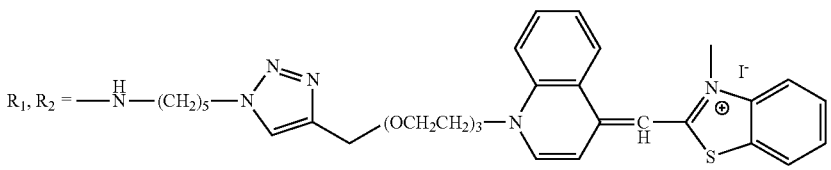 |
| 71 | 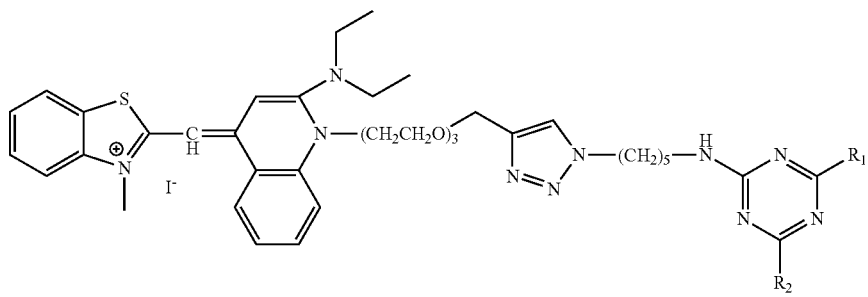 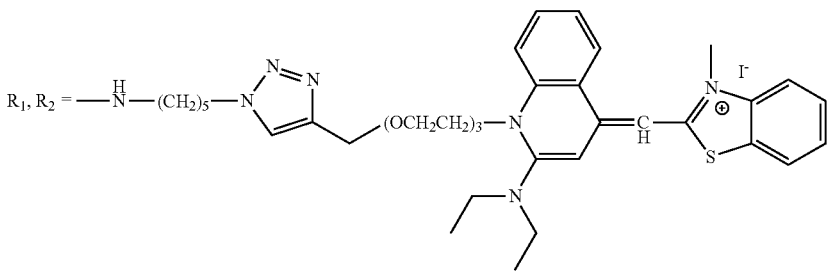 |
| 72 | 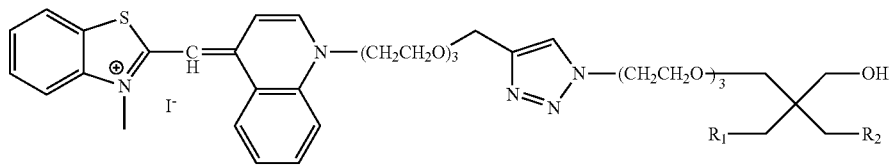 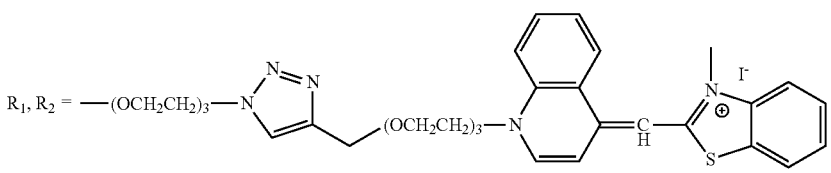 |

In some embodiments, the tetramers of the substituted unsymmetrical cyanine dyes of the invention are linked by a bridge between four cyanine dye units. The tetramer structures generally have the formula:

The subscripts n, which determine the length of each dye unit, are 0, 1, or 2. Changing the length of the dye units will affect the spectral properties of the dye units and of the tetramer.

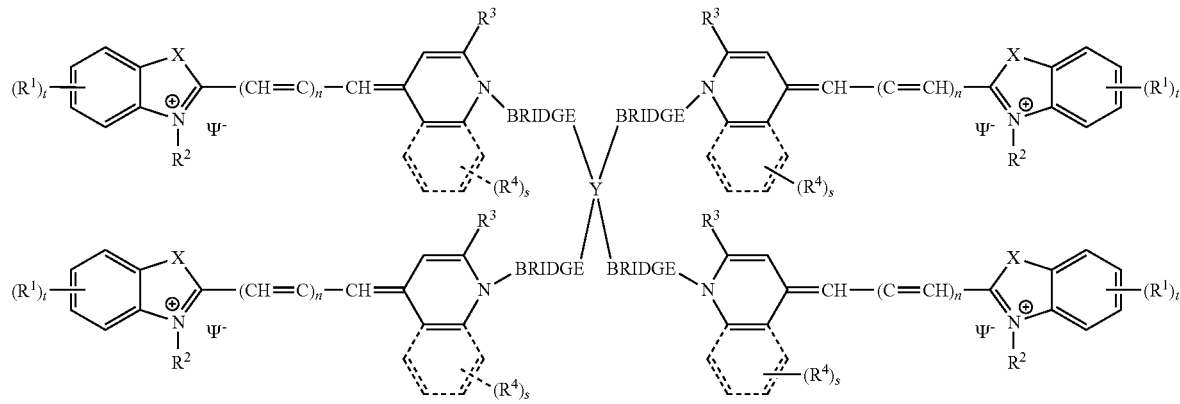

Groups $R^1$ and $R^4$ can independently comprise or be hydrogen, carboxy, sulfo, phosphate, phosphonate, hydroxyl, halogen, CN, amino, alkylamino, dialkylamino, alkoxy, alkyl, aryl, heteroaryl, alkylaminocarbonyl, dialkylaminocarbonyl, alkylaminosulfon-amide, dialkylaminosulfonamide, alkyl group substituted by a carboxy, alkyl group substituted by a sulfo, alkyl group substituted by a phosphate, $-Y-(CH_2)_a[O-(CH_2)_b]_o-O-Z$, where Y is absent, O, NH(C=O), C(=O)NH, or S(=O)$_2$NH; Z is H, alkyl, carboxy, sulfo, phosphate; each of a and b is an integer from 1 to 4; o is an integer selected from 1 to 12. Preferably the substitutes $R^1$ is hydrogen, carboxy, sulfo, or CN. Preferably the substitutes $R^4$ is hydrogen, methyl, or methoxyl.

Groups $R^2$ can comprise or be a substituted alkyl, unsubstituted alkyl, substituted arylalkyl, unsubstituted arylalkyl, substituted heteroalkyl, unsubstituted heteroalkyl, alkoxy, alkyl group substituted by a carboxy, a sulfo, a phosphate, an alkylamino, a dialkylamino, an alkylaminocarbonyl, a dialkylamino-carbonyl, an alkylaminosulfonamide, a dialkylaminosulfonamide, $-Y-(CH_2)_a[O-(CH_2)_b]_m-O-Z$, where Z is H, alkyl, carboxy, sulfo, phosphate; each of a and b is an integer from 1 to 4; o is an integer selected from 1 to 12. Preferably the substitutes $R^2$ is alkyl containing 1-3 carbons. More preferably, $R^2$ is methyl groups.

Groups $R^3$ can comprise or be H, substituted alkyl, unsubstituted alkyl, substituted heteroalkyl, unsubstituted heteroalkyl, substituted arylalkyl, unsubstituted arylalkyl, substituted aryl, unsubstituted aryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio. Preferably the substitutes $R^3$ is alkyl having 1-6 carbons, aryl, alkylamino, dialkylamino.

X can be one of O, S, or C(CH$_3$)$_2$. In preferred embodiments, X is O, or S.

The counterion ψ– is a biologically compatible ion that is stable and synthetically accessible. As used herein, a substance that is biologically compatible is not toxic as used, and does not have a substantially deleterious effect on biomolecules. Examples of ψ– include, among others, chloride, bromide, iodide, sulfate, phosphate, perchlorate, tetrafluoroborate, nitrate, and anions of aromatic or aliphatic carboxylic acids. Preferred ψ– counterions are chloride, iodide, sulfate, perchlorate.

The BRIDGE linking the two dye units, which may be charged or neutral, is a flexible linker molecule containing 4 to 40 non-hydrogen atoms. The linker contains at least one of heteroatoms N, O, or S, which may be the same or different.

-BRIDGE- has the general formula:

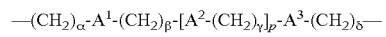

$$-(CH_2)_\alpha\text{-}A^1\text{-}(CH_2)_\beta\text{-}[A^2\text{-}(CH_2)_\gamma]_p\text{-}A^3\text{-}(CH_2)_\delta-$$

The subscripts α, β, γ, and δ, which may be the same or different, indicate the size of alkyl units, which contain from 1 to 12 carbon atoms each. The subscript p indicates the size of that unit, which may range from 1 to 12. $A^1$, $A^2$ and $A^3$, which may be the same or different, are independently O, S, CH$_2$, NR$^{12}$, where $R^{12}$ is H or an alkyl group having 1-6 carbons, N$^+$R$^{13}$R$^{14}$, where $R^{13}$ and $R^{14}$, which may be the same or different, are independently hydrogen or alkyl group having 1-6 carbons, C(=O)NR$^{15}$, where $R^{15}$ is H or an alkyl group having 1-6 carbons, or triazole. In a preferred embodiment, $A^1$ and $A^3$ are NR$^{12}$, C(=O)NR$^{15}$ or triazole, $A^2$ is O. More preferably, $R^{12}$ and $R^{15}$ are H.

Y is a scaffold.

Certain nonlimiting exemplary tetramers of substituted unsymmetrical cyanine dye are shown in Tables 4.

| Compound | Structure |
|---|---|
| 73 | (structure shown) |
| 74 | (structure shown) |

While many of the structures shown in Table 1, 2, 3 and 4 show one or more iodide anion(s), any other appropriate anion(s), such as those described herein, such as chloride anion(s), merely by way of example, may be used in place of the iodie anions shown.

In some embodiments, the dyes of this invention have absorption wavelength in the range from about 420 nm to about 750 nm, however the dyes generally provide only a negligible fluorescence emission peak unless bound to nucleic acids. Upon binding with DNA or RNA, the optical properties of the dyes change significantly. The fluorescence intensity of the dyes in the bound state is generally over 100 fold brighter than unbound state. In particular, the absorption curve typically shifts to a longer wavelength. Typically, the absorption curve shift is between about 5 nm and about 20 nm. Generally, the bound dye of this invention have a Stokes shift of between about 15 nm and about 20 nm.

In some embodiments, the change of spectral properties when the dye is bound to nucleic acids can be used to quantitatively or qualitatively analysis the presence or the amount of nucleic acids in a sample. To analysis the nucleic acids in a sample, the dye in a buffered solution is added to the sample thought to contain nucleic acids. Measurement of fluorescence or absorbance of the solution before and after the combination of the sample with nucleic acids are compared. The fluorescence intensity of the nucleic acid-dye complex is proportional to the amount of nucleic acid in the sample. Alternatively, the absorbance of solutions with and without the addition of nucleic acids can be compared.

In some embodiments, the change of fluorescence intensity can be used to qualitatively measure the activity of enzymes, such as DNAase that hydrolyses the nuleic acids, for example, and the changes of nucleic acids in a sample. The fluorescence of the solution containing dye and nucleic acids is compared with the fluorescence of the solution after the addition of a hydrolyzing enzyme.

In some embodiments, the dyes of this invention can be used as nucleic acid stains in cells. Because different dyes have different cell membrane permeability, the dyes with cell permeant can be used for living cell stains, and the dyes with cell impermeant can be used for dead or fixed cell stains. Besides, the dyes can be used to measure the viability of cells in the sample. Cell death or toxicity usually results in loss of cell membrane integrity. When the cell membrane is damaged, the nucleic acids inside the cell become accessible to the dyes with cell impermeant. By choosing one dye with cell permeant and another dye with cell impermeant and different emission wavelength, the live/dead cells can be differentiated based on fluorescence signals at two different emission wavelengths.

In some embodiments, the intensity of fluorescence can be used to measure the effect of a cytotoxic event including exposure to a chemical reagent, the addition of a biological agent, or other change in environmental condition that results in membrane disruption. The effect of a cytotoxic event can be observed over time, or after a fixed period of time. To measure the effect of a cytotoxic event that involves the addition of a cytotoxic reagent, a stock solution of the reagent is prepared at a concentration greater that what is expected to be a toxic dose and this is added to the cells or tissue in a suitable medium. Typically various concentrations of the reagent are added from 0 to greater than a toxic dose. Toxicity can be measured by the fluorescence intensity of cells after addition of the dyes.

In some embodiments, the dyes of this invention can be used for detection of nucleic acids immobilized relative to a matrix or a surface, or as nucleic acid gel stains. There are generally two methods for staining nucleic acids in gels using the dyes. The first method is post-gel staining, wherein a nucleic acid sample is separated by gel electrophoresis, the gel comprising the separated nucleic acids is incubated in a solution comprising the dye, the gel may be destained, if desirable or necessary to remove background fluorescence, and the resulting gel is viewed using a transiluminator or laser scanner. The second method is pre-cast gel staining, wherein a gel is premixed or pre-embedded with the dye, the nucleic acid sample is separated by electrophoresis using the pre-cast gel, and the stained gel is viewed using a transiluminator or laser scanner. In general, the dyes of this invention can be used for post-gel staining, pre-cast gel staining, or variations thereof.

In some embodiments, the dyes of this invention may be included in a kit. A kit may comprise the dye, information or a protocol regarding use of the dye or the kit, and/or other useful or necessary materials or reagents, such as any materials or reagents suitable for the detection of nucleic acids, for example, such as a buffer, a detergent, a DNA or RNA standard, a DNA or RNA ladder, and/or matrix.

EXAMPLES

The examples discussed below are intended to be purely exemplary of the invention and should not be considered to limit the invention in any way. The examples are not intended to represent that the experiments below are all or the only experiments performed.

Example 1

Preparation of Compound (75)

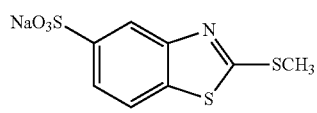

5 g of 2-methylthio-benzothiazole in 20 mL chlorosulfonic acid was stirred at room temperature overnight. The reaction mixture was added dropwise to 250 mL ice/water with stirring. The resulting white precipitate was collected by filtration, and washed with water. Then the white solid was suspended in 50 mL water, and 20 mL of 10% NaOH solution was added. The reaction mixture was stirred at room tempera-ture overnight. The white precipitate was collected by filtration, and stirred in 100 mL MeOH for 4 h, filtered and dried to give compound 75.

Example 2

Preparation of Compound (76)

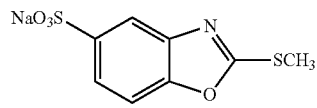

Compound 76 was prepared in a method analogous to that of compound 75, above.

Example 3

Preparation of Compound (77)

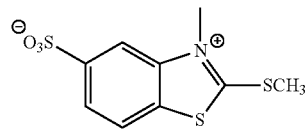

5 mmol of compound 75 and 15 mmol of methyl p-toluenesulfonate in 10 mL chlorobenzene were heated at 120° C. overnight. Then 20 mL ethyl acetate was added, and resulting mixture was refluxed for 30 min. The compound 77 was recovered by filtration as a white solid.

Example 4

Preparation of Compound (78)

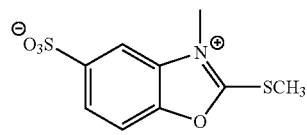

Compound 78 was prepared in a method analogous to that of compound 77, above.

Example 5

Preparation of Compound (79)

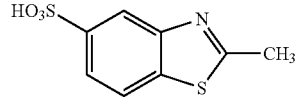

5 g of 2-Methyl benzothiazole was added dropwise to 10 mL of conc. $H_2SO_4$ at 0° C. 10 mL of fuming sulfuric acid (30% $SO_3$) was added dropwise, followed by addition of $FeCl_3$ (23 mg) at 0° C. The reaction mixture was stirred at 125° C. for 1 h. After cooling to room temperature, the mixture was added dropwise to cold acetone (~80 mL) with stirring. The resulting white precipitate was collected by filtration, and crystallized in MeOH/Ethyl acetate to give compound 79.

Example 6

Preparation of Compound (80)

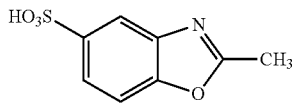

Compound 80 was prepared in a method analogous to that of compound 79, above.

Example 7

Preparation of Compound (81)

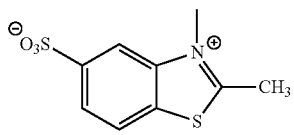

5 mmol of compound 79 and 15 mmol of methyl p-toluenesulfonate in 10 mL chlorobenzene were heated at 120° C. overnight. Then 20 mL ethyl acetate was added, and resulting mixture was refluxed for 30 min. The compound 81 was recovered by filtration as a white solid.

Example 8

Preparation of Compound (82)

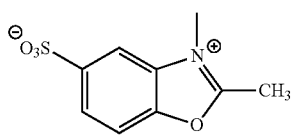

Compound 82 was prepared in a method analogous to that of compound 81, above.

Example 9

Preparation of Compound (83)

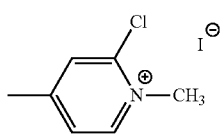

g of 2-Chloro-4-methylpyridine in 10 mL methyl iodide in a sealed tube was heated at 100° C. overnight. Then 30 mL ethyl acetate was added, and resulting mixture was refluxed for 30 min. The compound 83 was recovered by filtration as a white solid.

Example 10

Preparation of Compound (84)

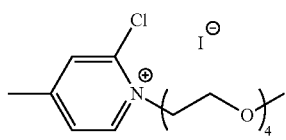

2 g of 2-Chloro-4-methylpyridine and 6 g of 2,5,8,11-tetraoxamidecan-13-yl 4-methylbenzenesulfonate in 20 mL chlorobenzene was heated at 120° C. overnight. Then 30 mL ethyl acetate was added, and resulting mixture was refluxed for 30 min. The supernatant was decanted and the residue was dried to give compound 84.

Example 11

Preparation of Compound (85)

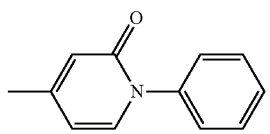

5 g of 2-Hydroxy-4-methylpyridine, 6.3 g of potassium carbonate, 14 g of iodobenzene, and 17 g of copper power in 80 mL DMF was heated at reflux overnight. The reaction mixture was cooled to room temperature, partitioned between water and ethyl acetate, filtered, and the organic layer was dried over $Na_2SO_4$. The crude product was purified on a silica gel column to yield compound 85.

Example 12

Preparation of Compound (86)

5 g of compound 85 in 100 mL dichloroethane was added with 12 g of phosphorus oxychloride. The reaction mixture was heated at 70° C. overnight. The mixture was concentrated to dryness under vacuum to give compound 86.

Example 13

Preparation of Compound (87)

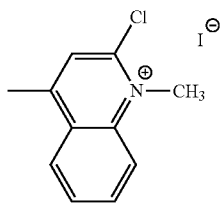

5 g of 2-Chlorolepidine in 10 mL methyl iodide in a sealed tube was heated at 100° C. overnight. Then 30 mL ethyl acetate was added, and resulting mixture was refluxed for 30 min. The compound 87 was recovered by filtration as a white solid.

Example 14

Preparation of Compound (88)

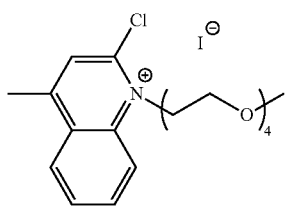

2 g of 2-Chlorolepidine and 4 g of 2,5,8,11-tetraoxamidecan-13-yl 4-methylbenzenesulfonate in 20 mL chlorobenzene was heated at 120° C. overnight. Then 30 mL ethyl acetate was added, and resulting mixture was refluxed for 30 min. The supernatant was decanted and the residue was dried to give compound 88.

Example 15

Preparation of Compound (89)

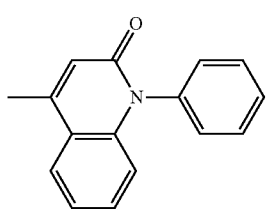 [SMILES: Cc1cc(=O)n(-c2ccccc2)c2ccccc12]

7.3 g of 2-Hydroxy-4-methylquinoline, 6.3 g of potassium carbonate, 14 g of iodobenzene, and 17 g of copper power in 80 mL DMF was heated at reflux overnight. The reaction mixture was cooled to room temperature, partitioned between water and ethyl acetate, filtered, and the organic layer was dried over $Na_2SO_4$. The crude product was purified on a silica gel column to yield compound 89.

Example 16

Preparation of Compound (90)

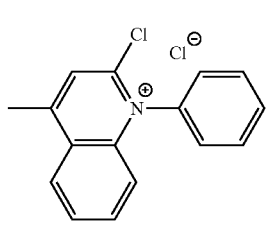 [SMILES: Cc1cc(Cl)[n+](-c2ccccc2)c2ccccc12 ; [Cl-]]

6 g of compound 89 in 100 mL dichloroethane was added with 12 g of phosphorus oxychloride. The reaction mixture was heated at 70° C. overnight. The mixture was concentrated to dryness under vacuum to give compound 90.

Example 17

Preparation of Compound (91)

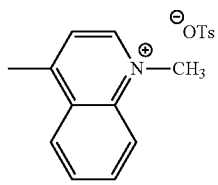

5 g of lepidine and 10 g of methyl p-toluenesulfonate in 20 mL chlorobenzene was heated at 120° C. overnight. Then 30 mL ethyl acetate was added, and resulting mixture was refluxed for 30 min. The compound 91 was recovered by filtration as a white solid.

Example 18

Preparation of Compound (92)

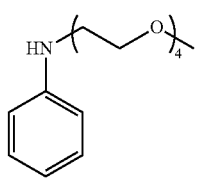

2 g of aniline, 7.8 g of 2,5,8,11-tetraoxamidecan-13-yl p-toluenesulfonate, and 3 g of potassium carbonate in 50 mL acetonitrile was heated at reflux overnight. The reaction mixture was concentrated, and partitioned between water and dichloromethane, and the organic layer was dired over Na$_2$SO$_4$. The crude product was purified on a silica gel column to yield compound 92.

Example 19

Preparation of Compound (93)

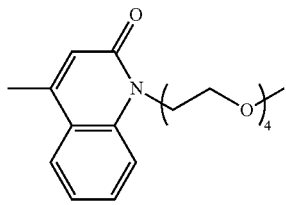

4 g of compound 92, and 2.4 g of 2,2,6-trimethyl-4H-1,3-dioxin-4-one in 20 mL xylene was heated at 145° C. for 1 hour. The reaction mixture was concentrated to dryness under high vacuum. The resulting residue was dissolved in 15 mL acetic acid and 15 mL conc. H$_2$SO$_4$. The reaction mixture was heated at 50° C. overnight. The reaction mixture was cooled to room temperature, partitioned between water and ethyl acetate, filtered, and the organic layer was dried over Na$_2$SO$_4$. The crude product was purified on a silica gel column to yield compound 93.

Example 20

Preparation of Compound (94)

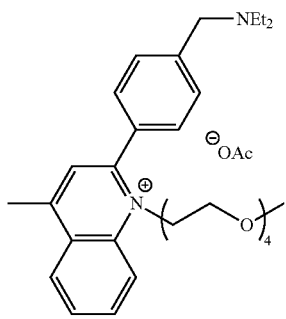

5 g of N,N-(4-bromobenzyl)diethylamine (20.6 mmol) was dissolved in 30 mL dry THF and cooled to −78° C. in a dry ice/acetone bath. 10 mL of n-butyllithium (1.6 M in hexane, 16 mmol) was added at −78° C., followed by addition of compound 93 (2.2 g, 10 mmol). After addition, the reaction mixture was stirred at −78° C. for 1 hour. Then, 5 mL of acetic acid was added, and the reaction mixture was warmed to room temperature, and stirred for another 2 hours. The mixture was concentrated to dryness under high vacuum to give crude compound 94.

Example 21

Preparation of Compound (95)

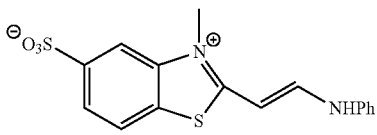

5 g of compound 81 (20.6 mmol), and 4.4 g of N,N'-diphenylformamidine (22.6 mmol) were dissolved in 10 mL acetic acid. 2.1 g of acetic anhydride (20.6 mmol) was added, and the reaction mixture was refluxed for 1 h. Then, 50 mL of ethyl acetate was added to the stirring mixture. The yellow precipitate was collected by filtration, and washed with ethyl acetate to give compound 95.

Example 22

Preparation of Compound (96)

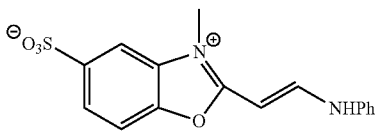

Compound 96 was prepared in a method analogous to that of compound 95, above.

Example 23

Preparation of Compound (97)

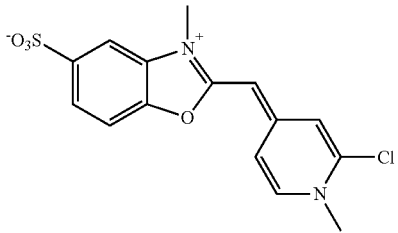

Compound 78 (2 mmol) and compound 83 (2 mmol) were dissolved in 5 mL dichloromethane. Triethylamine (5 mmol) was added, and the reaction mixture was stirred at room temperature for 2 hours. Then, ethyl acetate was added to the stirring mixture, and the yellow solid was collected by filtration, and washed with ethyl acetate, and dried to give compound 97.

Example 24

Preparation of Compound (1)

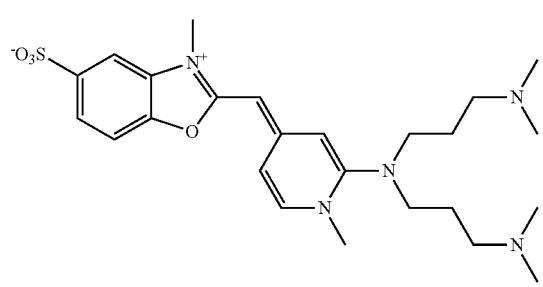

Compound 97 (1 mmol) and 3,3'-iminobis(N,N-dimethylpropylamine) (2 mmol) were dissolved in 10 mL dichloroethane. The reaction mixture was stirred at 50° C. for 2 hours. Then, ethyl acetate was added to the stirring mixture, and the yellow solid was collected by filtration, and washed with ethyl acetate, and dried to give compound 1.

Example 25

Preparation of Compounds (2-6)

Compounds 2-6 was prepared in a method analogous to that of compound 1, above.

Example 26

Preparation of Compound (7)

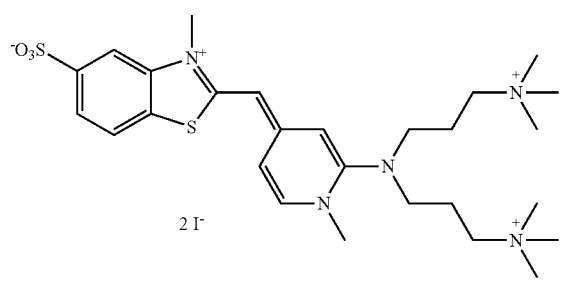

Compound 2 (1 mmol) and iodomethane (10 mmol) in 10 mL DMF were stirred at 60° C. for 2 hours. Then, ethyl acetate was added to the stirring mixture, and the solid was collected by filtration. Then the solid was triturated in ethyl acetate, acetone, and acetonitrile. The orange solid was collected by filtration and dried in vacuo to give compound 7.

Example 27

Preparation of Compound (98)

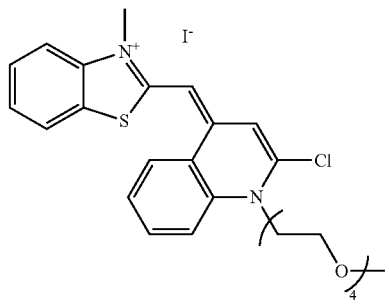

Compound 88 (2 mmol) and 3-methyl-2-(methylthio)benzothiazolium iodide (2 mmol) were dissolved in 5 mL dichloromethane. Triethylamine (5 mmol) was added, and the reaction mixture was stirred at room temperature for 2 hours. Then, ethyl acetate was added to the stirring mixture, and the yellow solid was collected by filtration, and washed with ethyl acetate, and dried to give compound 98.

Example 28

Preparation of Compound (36)

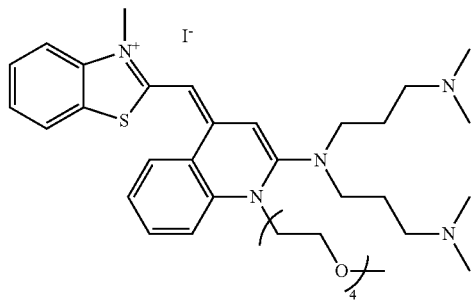

Compound 98 (1 mmol) and 3,3'-iminobis(N,N-dimethylpropylamine) (2 mmol) were dissolved in 10 mL dichloroethane. The reaction mixture was stirred at 50° C. for 2 hours. Then, ethyl acetate was added to the stirring mixture, and the yellow solid was collected by filtration, and washed with ethyl acetate, and dried to give compound 36.

Example 29

Preparation of Compound (40)

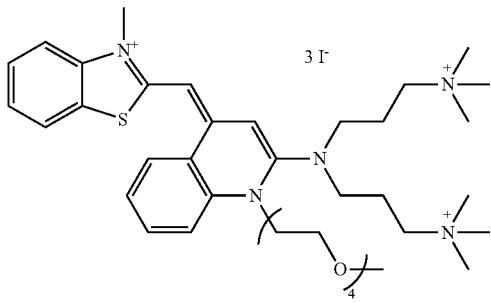

Compound 36 (1 mmol) and iodomethane (10 mmol) in 10 mL DMF were stirred at 60° C. for 2 hours. Then, ethyl acetate was added to the stirring mixture, and the solid was collected by filtration. Then the solid was triturated in ethyl acetate, acetone, and acetonitrile. The orange solid was collected by filtration and dried in vacuo to give compound 40.

Example 30

Preparation of Compound (39)

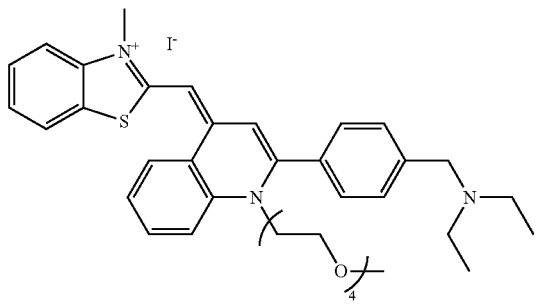

Compound 94 (2 mmol) and 3-methyl-2-(methylthio)benzothiazolium iodide (2 mmol) were dissolved in 5 mL dichloromethane. Triethylamine (5 mmol) was added, and the reaction mixture was stirred at room temperature for 2 hours. Then, ethyl acetate was added to the stirring mixture, and the yellow solid was collected by filtration, and washed with ethyl acetate, and dried to give compound 39.

Example 31

Preparation of Compound (42)

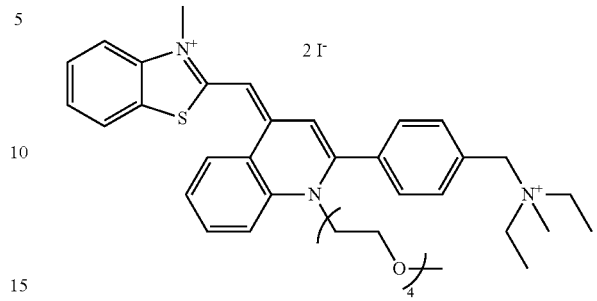

Compound 39 (1 mmol) and iodomethane (5 mmol) in 5 mL DMF were stirred at 60° C. for 2 hours. Then, ethyl acetate was added to the stirring mixture, and the solid was collected by filtration. Then the solid was triturated in ethyl acetate, acetone, and acetonitrile. The orange solid was collected by filtration and dried in vacuo to give compound 42.

Example 32

Preparation of Compound (51)

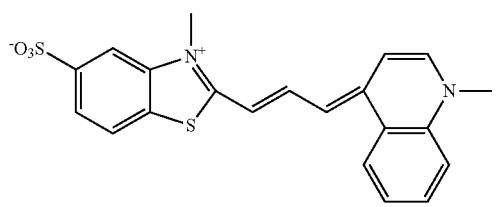

Compound 91 (1 mmol) and compound 95 (1 mmol) were dissolved in 5 mL dichloromethane. Triethylamine (5 mmol) and acetic anhydride (1 mmol) were added, and the reaction mixture was stirred are room temperature for 2 hours. Then, ethyl acetate (25 mL) was added to the stirring mixture, and the blue solid was collected by filtration. Then the solid was triturated in ethyl acetate, acetone, and acetonitrile. The blue solid was collected by filtration and dried in vacuo to give compound 51.

Example 33

Preparation of Compound (99)

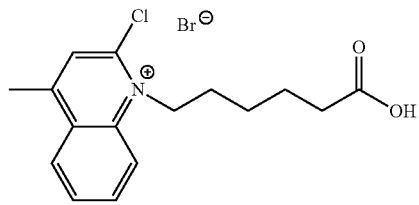 [SMILES: Cc1cc(Cl)[n+](CCCCCC(=O)O)c2ccccc12 ; [Br-]]

2 g of 2-Chlorolepidine and 2.2 g of 6-bromocaproic acid in 20 mL chlorobenzene was heated at 120° C. overnight. Then 30 mL ethyl acetate was added, and resulting mixture was refluxed for 30 min. The supernatant was decanted and the residue was dried to give compound 99.

Example 34

Preparation of Compound (100)

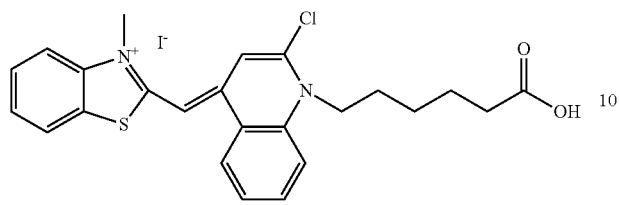

Compound 99 (2 mmol) and 3-methyl-2-(methylthio)benzothiazolium iodide (2 mmol) were dissolved in 5 mL dichloromethane. Triethylamine (5 mmol) was added, and the reaction mixture was stirred at room temperature for 2 hours. Then, ethyl acetate was added to the stirring mixture, and the yellow solid was collected by filtration, and washed with ethyl acetate, and dried to give compound 100.

Example 35

Preparation of Compound (101)

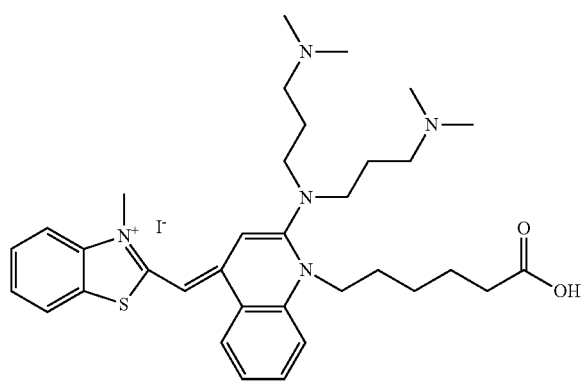 [SMILES: CN(C)CCCN(CCCN(C)C)C1=C/C(=C\c2sc3ccccc3[n+]2C)c2ccccc2N1CCCCCC(=O)O ; [I-]]

Compound 100 (1 mmol) and 3,3'-iminobis(N,N-dimethylpropylamine) (2 mmol) were dissolved in 10 mL dichloroethane. The reaction mixture was stirred at 50° C. for 2 hours. Then, ethyl acetate was added to the stiffing mixture, and the yellow solid was collected by filtration, and washed with ethyl acetate, and dried to give compound 101.

Example 36

Preparation of Compound (61)

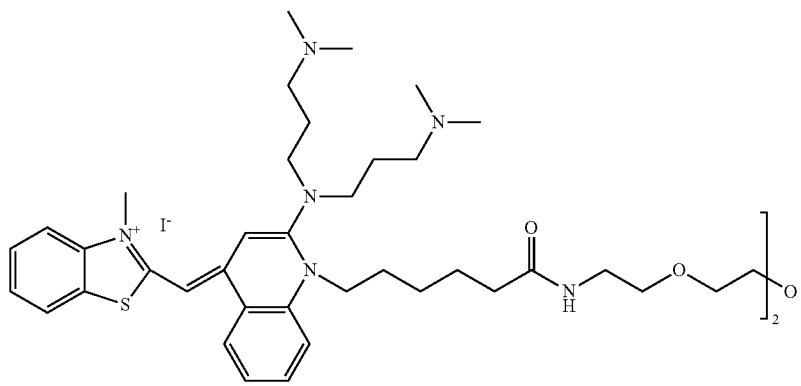 [SMILES: CN(C)CCCN(CCCN(C)C)C1=C/C(=C\c2sc3ccccc3[n+]2C)c2ccccc2N1CCCCCC(=O)NCCOCCO ; [I-]]

Compound 101 (1 mmol) was suspended in 5 mL DMF. TSTU (1 mmol) and triethylamine (1 mmol) were added. The reaction mixture was stirred at room temperature for 30 min. Then 4,7,10-trioxa-1,13-tridecanediamine (0.5 mmol) was added, and the reaction mixture was stirred at room temperature overnight. Ethyl acetate (20 mL) was added to the stiffing mixture, and the yellow solid was collected by filtration. The solid was redissolved in DMF and precipitated out again with ethyl acetate, and dried to give compound 61.

Example 37

Stability Test of Compound (39) and SYBR Gold in TBE Buffer

SYBR Gold 10,000× in DMSO from Invitrogen was diluted to 2× working concentration in 1×TBE buffer. Compound 39 was prepared in 2 μM solution in 1×TBE buffer. Equal amount of salmon sperm DNA (50 μg/mL) was added to above solutions of SYBR Gold and compound 39. The fluorescence intensity associated with each of the solutions was monitored at excitation wavelength 480 nm and emission wavelength 520 nm over the course of different time period at room temperature. A graphical representation of normalized fluorescence intensity versus time for each of the solutions is shown in FIG. 1. As shown, compound 39 is very stable in aqueous solution, while SYBR Gold is decomposed very fast in aqueous solution. This demonstrates that compound 39 is more stable than SYBR Gold, as preciously described herein.

Example 38

Selectivity Test of Compound (36), Compound (40) and Compound (49) on dsDNA, ssDNA, and RNA in TE Buffer Compound 36, compound 40, and compound 49 were prepared in 2 μM concentration in 1×TE buffer, individually. Salmon sperm dsDNA, calf thymus ssDNA, and *E. coli* rRNA were prepared in 10 μg/mL concentration in 1×TE buffer, individually. Equal amount of each solution of dsDNA, ssDNA, and RNA was added to the solutions of compound 36, compound 40 and compound 49, individually. The emission spectrum associated with each of the solutions was scanned at excitation wavelength 480 nm for compound 36 and 40, and at excitation wavelength 620 nm for compound 49. A graphical representation of emission spectra is shown in FIG. 2. As shown, compound 36 has good selectivity for dsDNA versus ssDNA or RNA, and compound 40 has good selectivity for DNA versus RNA, while compound 49 is selective for RNA versus DNA.

Example 39

Quantitation of DNA, and RNA in Solution

Compound 36, and compound 49 were prepared in 100 μM stock solution in 1×TE buffer, individually. Calf thymus DNA, and *E. coli* rRNA were prepared in 50 μg/mL stock solution in 1×TE buffer, individually. Calf thymus DNA, and *E. coli* rRNA were diluted into 0, 0.25, 0.5, 1, 2, 3, 4, 5 μg/mL final concentrations. Compound 236 and 49 were added at final concentration 1 μM. The fluorescence intensity was measured on fluorescence plate reader using excitation wavelength at 480 nm and emission detection wavelength at 520 nm for compound 36, and excitation wavelength at 620 nm and emission detection wavelength at 660 nm for compound 49. Fluorescence intensity was plotted against DNA and RNA concentrations, as shown in FIG. 3. As shown, compound 36 has nice linear response for DNA versus RNA, while compound 49 is linear response for RNA versus DNA.

Example 40

DNA Gel Staining

Agarose gels (1% agarose) were prepared according to a standard protocol. Serial two-fold dilutions of 1 kb plus DNA Ladder from Invitrogen were prepared, and the resulting DNA samples were loaded onto an agarose gel. The DNA samples were electrophoretically separated in 1×TBE buffer using a standard protocol. A stock solution of each compound 39, compound 65, and SYBR Safe (10,000×) from Invitrogen were diluted into ~1 μM final concentration in 1×TE buffer, respectively. The agarose gels were incubated in the staining solutions for ~30 min to stain the gels. The resulting gel was then viewed using UV transilluminator. Photographs of the fluorescent images of the illuminated gels were taken with a SYBR filter and CCD camera, as shown in FIG. 4. As shown, compounds 39 and 65 are more sensitive than SYBR Safe.

Example 41

Celluar Nucleic Acid Staining

Compound 38, compound 42, and compound 61 were prepared in 1 mM stock solution in water, respectively. Each compound at 1 μM concentration in PBS buffer was incubated with live and fixed HeLa cells in 96-well plate for 10 min, respectively. The fluorescence imaging of cells was taken on a fluorescence microscopy with a 488 nm excitation laser and a 520±15 nm emission filter, as shown in FIG. 5. As shown, compound 38 is live cell permeant, while compound 42 and 61 are live cell impermeant.

The invention claimed is:

1. A compound having the formula:

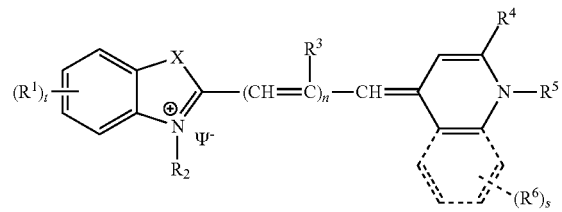

wherein:
X is O, S, or $C(CH_3)_2$;
Each of $R^1$ or $R^6$ is independently hydrogen, carboxy, sulfo, halogen, CN, or alkoxy;
Each of t and s is an integer from 0 to 4;
$R^2$ is an alkyl, or alkyl group substituted by a carboxy, a sulfo, or a phosphate;
$R^3$ is H, or $C_6H_4CH_2N(CH_2CH_3)_2$;
$R^4$ is H, alkyl, heteroalkyl, arylalkyl, aryl, cycloalkyl, heterocycloalkyl, halogen, alkoxy, alkylamino, or alkylthio;
$R^5$ is —$(CH_2)_a$—[O—$(CH_2)_b]_m$—O—Z, where Z is H, alkyl, carboxy, sulfo, or phosphate; each of a and b is an integer from 1 to 4; m is an integer selected from 1 to 12;
n is 0, 1, or 2;
$\psi$– is $Cl^-$, $Br^-$, or $I^-$.

2. The compound according to claim 1, wherein X is O, or S.

3. The compound according to claim 2, wherein each of $R^1$ or $R^6$ is independently hydrogen, carboxy, sulfo, or halogen.

4. The compound according to claim 3, wherein $R^2$ is alkyl.

5. The compound according to claim 4, wherein $R^3$ is H.

6. The compound according to claim 5, wherein $R^4$ is H, alkyl, aryl, halogen, alkoxy, alkylamino, or alkylthio.

7. The compound according to claim 6, wherein n is 0 or 1.

8. The compound according to claim 7, wherein $R^5$ is —$(CH_2)_a$—[O—$(CH_2)_b]_m$—O—Z, where Z is H, or alkyl; each of a and b is an integer from 1 to 3; m is an integer selected from 1 to 6.

9. The compound according to claim 8, wherein $R^1$ is H or sulfo, $R^2$ is methyl or ethyl, $R^6$ is H or methoxyl, and $R^5$ is —$(CH_2)_a$—[O—$(CH_2)_b]_m$—O—Z, where Z is H, or methyl; each of a and b is an integer from 2 to 3; m is an integer selected from 1 to 6.

10. A kit for detecting nucleic acid in a sample, wherein the kit comprises a compound according to claim 1.

11. The compound according to claim 9, wherein X is S, $R^1$ is H, $R^2$ is methyl, $R^3$ is H, $R^4$ is H, or alkylamino, $R^5$ is —$(CH_2)_2$—[O—$(CH_2)_2]_3$—O—$CH_3$, and $R^6$ is H, n is 0.

* * * * *